(12) United States Patent
Kim et al.

(10) Patent No.: US 11,324,432 B2
(45) Date of Patent: May 10, 2022

(54) SIGNAL PROCESSING METHOD AND APPARATUS

(71) Applicants: Samsung Electronics Co., Ltd., Suwon-si (KR); The Industry & Academic Cooperation in Chungnam National University (IAC), Daejeon (KR)

(72) Inventors: JongPal Kim, Seoul (KR); TakHyung Lee, Suwon-si (KR); Hyoung Ho Ko, Daejeon (KR)

(73) Assignees: Samsung Electronics Co., Ltd., Suwon-si (KR); THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 261 days.

(21) Appl. No.: 16/182,786

(22) Filed: Nov. 7, 2018

(65) Prior Publication Data

US 2019/0069799 A1 Mar. 7, 2019

Related U.S. Application Data

(62) Division of application No. 14/715,949, filed on May 19, 2015, now Pat. No. 10,149,628.

(30) Foreign Application Priority Data

May 20, 2014 (KR) .......................... 10-2014-0060542
Feb. 5, 2015 (KR) .......................... 10-2015-0017881

(51) Int. Cl.
*A61B 5/024* (2006.01)
*A61B 5/00* (2006.01)
*A61B 5/304* (2021.01)
*A61B 5/24* (2021.01)
*A61B 5/30* (2021.01)
*A61B 5/316* (2021.01)

(52) U.S. Cl.
CPC .............. *A61B 5/304* (2021.01); *A61B 5/024* (2013.01); *A61B 5/24* (2021.01); *A61B 5/30* (2021.01); *A61B 5/316* (2021.01); *A61B 5/681* (2013.01); *A61B 5/7225* (2013.01)

(58) Field of Classification Search
CPC .......................... A61B 5/04288; A61B 5/7225
See application file for complete search history.

(56) References Cited

U.S. PATENT DOCUMENTS

| | | | |
|---|---|---|---|
| 5,748,132 A | 5/1998 | Matsuzawa | |
| 5,838,488 A | 11/1998 | Kobayashi | |
| 6,602,201 B1 | 8/2003 | Hepp et al. | |
| 7,203,536 B2 | 4/2007 | Masuo | |
| 7,622,988 B2 | 11/2009 | Denison et al. | |

(Continued)

FOREIGN PATENT DOCUMENTS

| | | | |
|---|---|---|---|
| KR | 10-2008-0088727 | * | 10/2008 |
| KR | 10-2008-0088727 A | | 10/2008 |

*Primary Examiner* — William J Levicky
(74) *Attorney, Agent, or Firm* — NSIP Law

(57) ABSTRACT

A signal processing apparatus includes an input voltage selector configured to select an input voltage from a plurality of input voltages; an input element connected to the input voltage selector; and an input current controller configured to control an inflow of an input current in conjunction with an operation of the input voltage selector.

6 Claims, 19 Drawing Sheets

(56) References Cited

U.S. PATENT DOCUMENTS

| | | |
|---|---|---|
| 7,738,947 B2 | 6/2010 | Chow et al. |
| 7,911,411 B2 | 3/2011 | Yoshikawa |
| 7,952,428 B2 | 5/2011 | Golden et al. |
| 8,138,830 B2 | 3/2012 | Bugyik |
| 8,179,195 B1 | 5/2012 | Huijsing et al. |
| 8,454,505 B2 | 6/2013 | Yazicioglu et al. |
| 2001/0010467 A1* | 8/2001 | Oguma .............. A61B 5/0537 324/601 |
| 2014/0358012 A1* | 12/2014 | Richards ............ A61B 5/6802 600/479 |
| 2019/0036497 A1* | 1/2019 | Kim .................... A61B 5/302 |

* cited by examiner

SIGNAL PROCESSING METHOD AND APPARATUS

CROSS-REFERENCE TO RELATED APPLICATION(S)

This application is a divisional of U.S. patent application Ser. No. 14/715,949 filed on May 19, 2015 which claims the benefit under 35 USC 119(a) of Korean Patent Application Nos. 10-2014-0060542 filed on May 20, 2014, and 10-2015-0017881 filed on Feb. 5, 2015, in the Korean Intellectual Property Office, the entire disclosures of which are incorporated herein by reference for all purposes.

BACKGROUND

1. Field

The following description relates to signal processing technology for processing an input signal and generating an output signal.

2. Description of Related Art

An instrumentation amplifier (IA) is used to measure various signals. For example, in a medical field, the IA may be used to measure and amplify a biosignal such as an electrocardiogram (ECG), an electromyogram (EMG), a photoplethysmogram (PPG), a bioimpedance, a movement signal, or any other biosignal.

In general, the IA may be implemented using a differential amplifier having a low offset, low noise, a high common-mode rejection, a high loop gain, and a high input resistance. The IA may include a chopper circuit to modulate a measured signal into a signal of a high-frequency band or demodulate the modulated signal into a signal of a low-frequency band.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a signal processing apparatus includes an input voltage selector configured to select an input voltage from a plurality of input voltages; an input element connected to the input voltage selector; and an input current controller configured to control an inflow of an input current in conjunction with an operation of the input voltage selector.

The signal processing apparatus may be configured to be operable in a voltage measuring mode and a current measuring mode.

The input voltage selector may be configured to apply a preset reference voltage to the input element in the current measuring mode, and apply an input voltage to be measured to the input element in the voltage measuring mode.

The preset reference voltage may have a fixed voltage level or a variable voltage level.

The input current controller may be configured to allow the inflow of the input current into the signal processing apparatus in the current measuring mode, and block the inflow of the input current in the voltage measuring mode.

The input element may be configured to generate a current in response to the selected input voltage in the voltage measuring mode.

The input current controller may include an input current compensator configured to output a compensation current to adjust a level of the input current in the current measuring mode.

The apparatus may further include an input current compensation controller configured to control a level of the compensation current output by the input current compensator based on an output signal of the signal processing apparatus.

The apparatus may further include a low-pass filter configured to extract a signal of a low-frequency band from an output signal of the signal processing apparatus and output the signal of the low-frequency band; a comparator configured to compare a level of the signal output by the low-pass filter to a level of a preset reference signal and output a signal indicating a result of the comparing; and an input current compensation controller configured to generate a control signal to control the input current compensator based on the signal output by the comparator.

The input current controller may include a chopper configured to modulate a frequency component of the input current based on a control signal in the current measuring mode.

The may further include a load element functionally connected to the input element and the input current controller.

An output end of the input current controller may be connected to both ends of the load element, and one end of the input element may be connected to one of the ends of the load element.

In another general aspect, a signal processing apparatus includes a voltage input circuit configured to receive an input voltage; a current input circuit configured to receive an input current; an amplifier configured to amplify one of the input voltage and the input current at a time; and a controller configured to control a connection between the voltage input circuit and the amplifier, and control a connection between the current input circuit and the amplifier.

The controller may be further configured to block the connection between the current input circuit and the amplifier and connect the voltage input circuit to the amplifier in a voltage measuring mode.

The controller may be further configured to block the connection between the voltage input circuit and the amplifier and connect the current input circuit to the amplifier in a current measuring mode.

The current input circuit may be further configured to adjust a level of the input current in response to the level of the input current being greater than a preset value and output the input current having the adjusted level in a current measuring mode.

The input voltage may be an electrocardiogram (ECG) signal, and the input current may be a photoplethysmogram (PPG) signal.

In another general aspect, a signal processing apparatus includes a light source unit configured to output a light signal to a body of a user; a light detector configured to detect a first biosignal measured based on the light signal; a bioelectrode configured to detect a second biosignal measured based on a voltage signal; a signal processor configured to amplify the first biosignal or the second biosignal based on a measurement mode; and a controller configured to control the measurement mode of the signal processor.

The signal processor may be further configured to be operable in a current measuring mode and a voltage measuring mode; and the controller may be further configured to control the signal processor to amplify the first biosignal in the current measuring mode, and control the signal processor to amplify the second biosignal in the voltage measuring mode.

The first biosignal may be a photoplethysmogram (PPG) signal, and the second biosignal may be an electrocardiogram (ECG) signal.

The light source unit may include a plurality of light sources; and the controller may be further configured to sequentially activate at least one light source among the light sources during each of a plurality of time intervals, and determine a light source for measuring the first biosignal from the light sources based on a level of a signal output from the light detector during each of the time intervals.

In another general aspect, a signal processing method includes selecting a voltage measuring mode or a current measuring mode; and controlling a type of an input voltage selected and an inflow of an input current based on a result of the selecting.

The controlling may include blocking the inflow of the input current and selecting a voltage to be measured as the input voltage in response to the voltage measuring mode being selected.

The controlling may include selecting a preset reference voltage as the input voltage and allowing the inflow of the input current in response to the current measuring mode being selected.

The controlling may include adjusting a level of the input current to be within a preset range.

In another general aspect, a non-transitory computer-readable storage medium stores instructions to cause a computer to perform the method described above.

In another general aspect, a signal processing apparatus includes an amplifier configured to receive a plurality of input voltages and an input current and including an amplifying circuit configured to amplify both a voltage and a current; and a controller configured to control the amplifier to amplify a selected one of the input voltages and the input current using the amplifying circuit.

The input voltages may include a voltage to be measured and a reference voltage; and the controller may be further configured to control the amplifier to block the input current from being applied to the amplifying circuit and apply the voltage to be measured to the amplifying circuit to measure the voltage to be measured in a voltage measuring mode, and apply the reference voltage and the input current to the amplifying circuit to measure the input current in a current measuring mode.

The amplifier may include a first chopper configured to selectively modulate the input current; the signal processing apparatus may further include a second chopper configured to selectively modulate the voltage to be measured, and a third chopper configured to selectively demodulate an output signal of the amplifier; and the controller may be further configured to control the first chopper to block the input current from being applied to the amplifying circuit in the voltage measuring mode, and apply the input current to the amplifying circuit in the current measuring mode.

The amplifying circuit may include a transconductance amplifier configured to output a current obtained by amplifying the selected one of the input voltages and the input current; and the signal processing apparatus may further include a transimpedance amplifier configured to amplify the output current of the transconductance amplifier and output a voltage obtained by amplifying the output current.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 1:
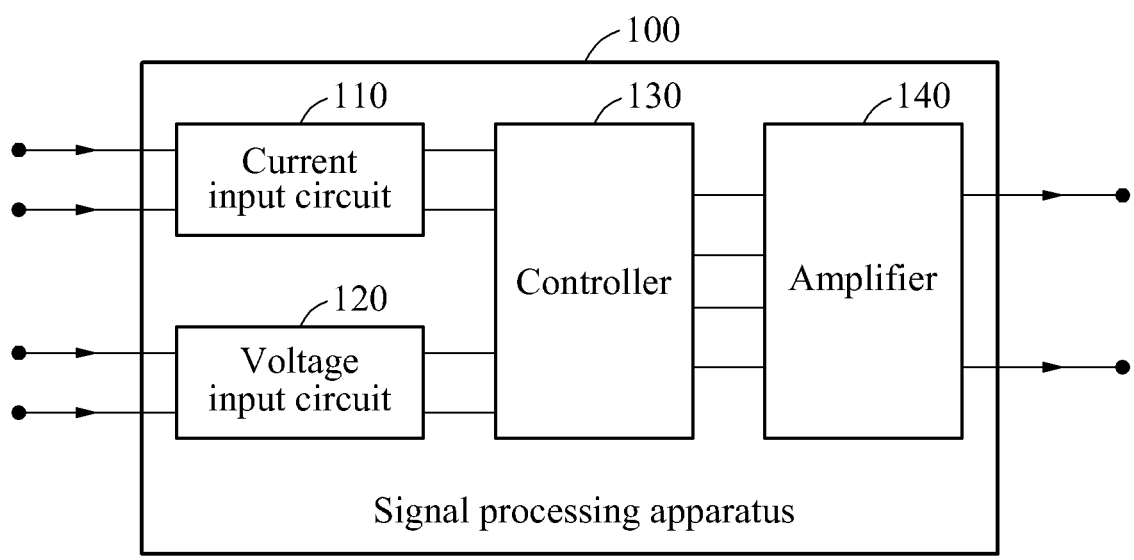
FIG. 1 is a diagram illustrating an example of an overall operation performed by a signal processing apparatus.

FIG. 1 is a diagram illustrating an example of an overall operation performed by a signal processing apparatus 100.

The signal processing apparatus 100 measures a current or a voltage for each channel in a multichannel environment. The signal processing apparatus 100 may operate in a voltage measuring mode, a current measuring mode, and a combination mode. The combination mode is a measurement mode that changes between the voltage measuring mode and the current measuring mode in response to a control signal. The signal processing apparatus 100 measures an input voltage and an input current using a single integral circuit configuration. The signal processing apparatus 100 provides compatibility between a voltage measurement and a current measurement by controlling processing of the input voltage and the input current input to a measurement circuit based on a control signal.

In one example, the signal processing apparatus 100 is included in an instrumentation amplifier (IA), and the IA uses the signal processing apparatus 100 to selectively measure the voltage and the current. For example, the IA including the signal processing apparatus 100 may amplify a voltage measurement-based biosignal such as an electrocardiogram (ECG), or a current measurement-based biosignal such as a photoplethysmogram (PPG). The signal processing apparatus 100 measures the ECG in the voltage measuring mode, and measures the PPG in the current measuring mode.

Referring to FIG. 1, the signal processing apparatus 100 includes a current input circuit 110, a voltage input circuit 120, a controller 130, and an amplifier 140.

The voltage input circuit 120 receives an input voltage. The input voltage may be, for example, an ECG signal measured from a body of a user. The current input circuit 110 receives an input current. As an example, the input current may be a biosignal including a blood oxygen saturation level, for example, peripheral capillary oxygen saturation ($SpO_2$), or a PPG signal measured from the body of the user.

The amplifier 140 amplifies either the input voltage or the input current under a control of the controller 130. The amplifier 140 amplifies the input voltage output from the voltage input circuit 120 or the input current output from the current input circuit 110 based on a measurement mode. The measurement mode is selected from the voltage measuring mode for measuring the input voltage and the current measuring mode for measuring the input current.

The controller 130 controls a connection between the voltage input circuit 120 and the amplifier 140 and a connection between the current input circuit 110 and the amplifier 140. For example, the controller 130 performs a switching operation to select a signal to be applied to the amplifier 140 from the input current and the input voltage. In the voltage measuring mode, the controller 130 blocks the connection between the current input circuit 110 and the amplifier 140, and connects the voltage input circuit 120 to the amplifier 140. Accordingly, the input current received by the current input circuit 110 is not input to the amplifier 140, and the input voltage output from the voltage input circuit 120 is input to the amplifier 140 to be amplified.

In the current measuring mode, the controller 130 blocks the connection between the voltage input circuit 120 and the amplifier 140, and connects the current input circuit 110 to the amplifier 140. Accordingly, the input voltage received by the voltage input circuit 120 is not input to the amplifier 140, and the input current output from the current input circuit 110 is input to the amplifier 140 to be amplified.

In the current measuring mode, when a level of the input current is greater than a preset value, the current input circuit 110 may adjust the level of the input current so that the level of the input current is less than the present value. The current input circuit 110 may generate a compensation current to adjust the level of the input current. The compensation current may compensate the input current so that the level of the input current is adjusted to be within an operational range of the signal processing apparatus 100.

Hereinafter, the operation of the signal processing apparatus 100 will be explained in detail.

Figure 2:
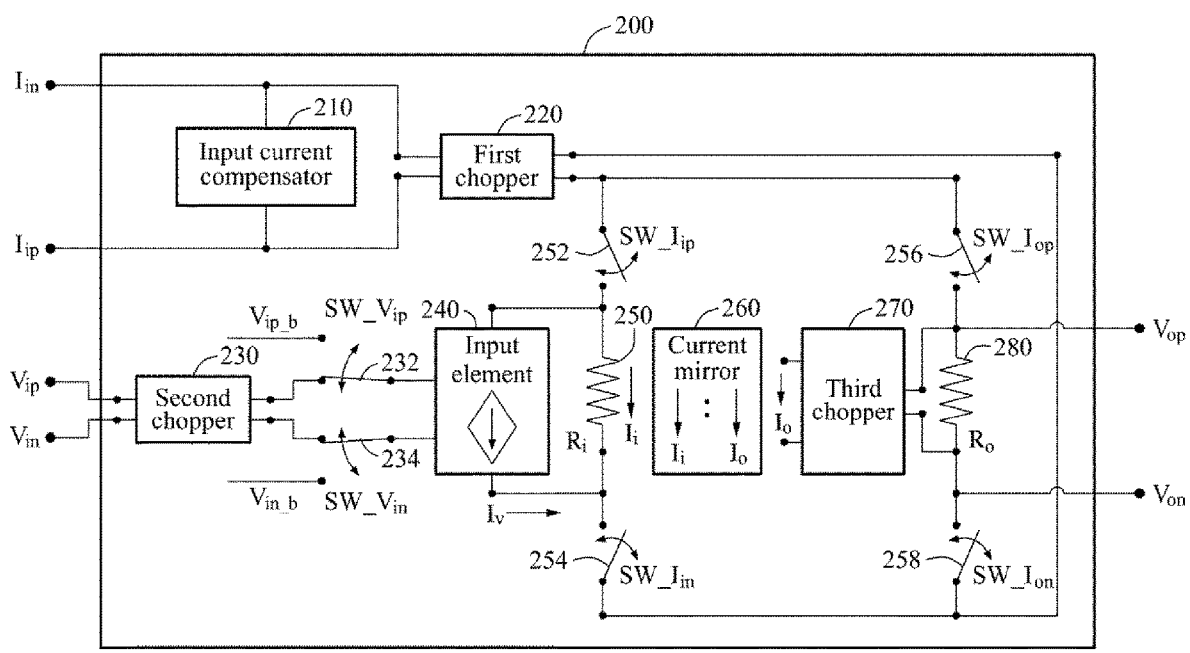
FIGS. 2 and 3 are diagrams illustrating an example of a circuit for implementing a signal processing apparatus.
Figure 3:
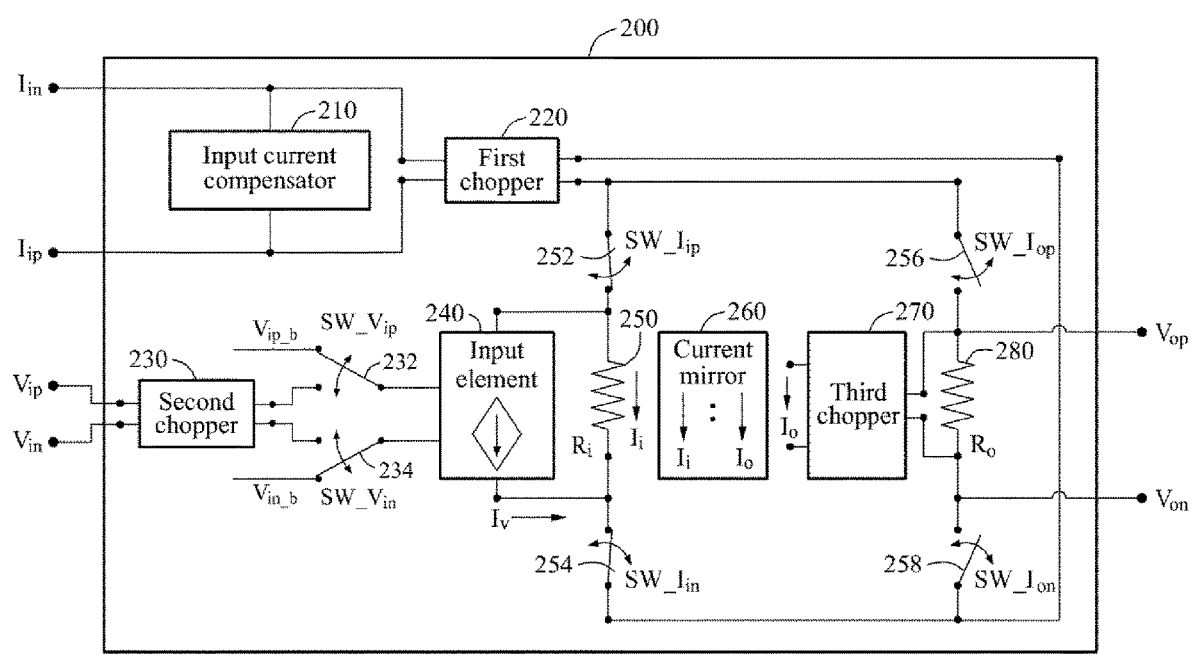

FIGS. 2 and 3 are diagrams illustrating an example of a circuit for implementing a signal processing apparatus 200.

Referring to FIGS. 2 and 3, the signal processing apparatus 200 measures an input voltage and an input current using a single integral circuit configuration. The signal processing apparatuses 100 and 200 control an input voltage and an input current input to a measuring circuit based on a control signal. FIG. 2 illustrates a switching connection performed by the signal processing apparatus 200 in a voltage measuring mode. FIG. 3 illustrates a switching connection performed by the signal processing apparatus 200 in a current measuring mode.

Hereinafter, the signal processing apparatus 200 operating in the voltage measuring mode and the signal processing apparatus 200 operating in the current measuring mode will be explained separately.

In the voltage measuring mode, the signal processing apparatus 200 operates as described below.

Referring to FIG. 2, when the signal processing apparatus 200 operates in the voltage measuring mode, the signal processing apparatus 200 controls switches SW_$I_{ip}$ 252, SW_$I_{in}$ 254, SW_$I_{op}$ 256, and SW_$I_{on}$ 258 configured to control a flow of input currents $I_p$ and $I_n$ in the signal processing apparatus 200 to be opened. The input currents $I_p$ and $I_n$ actually represent a single input current that flows into the signal processing apparatus 200 as the input current $I_p$, and flows out of the signal processing apparatus 200 as the input current $I_n$. Alternatively, the single input current may flow into the signal processing apparatus 200 as the input current $I_n$, and flow out of the signal processing apparatus 200 as the input current $I_p$.

The signal processing apparatus 200 controls switches SW_$V_{ip}$ 232 and SW_$V_{in}$ 234 configured to control a flow of input voltages $V_{ip}$ and $V_{in}$ to be measured in the signal processing apparatus 200 to be closed so that an output end of a second chopper 230 is connected to an input end of an input element 240. The signal processing apparatus 200 may control the second chopper 230 to output the input voltages $V_{ip}$ and $V_{in}$ directly, or to output the input voltages $V_{ip}$ and $V_{in}$ after converting a frequency component of the input voltages $V_{ip}$ and $V_{in}$. For example, the second chopper 230 may convert the frequency component of the input voltages $V_{ip}$ and $V_{in}$ to have a frequency higher or lower than an original frequency of the frequency component of the input voltages $V_{ip}$ and $V_{in}$. In one example, the input element 240 may be a voltage-current converter or a transistor. The input element 240 outputs a current based on a differential voltage between the input voltages $V_{ip}$ and $V_{in}$.

The current output $I_v$ from the input element 240 causes a current $I_i$ to flow through an input resistor 250, for example, $R_i$, constituting a load element. A current mirror 260 mirrors the current $I_i$ flowing through the input resistor 250 to output a current $I_o$ having a same level or an amplified level relative to the current $I_i$. The current $I_o$ output from the current mirror 260 generates voltages at both ends of an output resistor 280, for example, $R_o$. Based on the generated voltages, output voltages $V_{op}$ and $V_{on}$ are output from output terminals of the signal processing apparatus 200.

In another example, the current $I_o$ output from the current mirror 260 is input to a third chopper 270, and the third chopper 270 converts a frequency component of the current $I_o$. For example, the third chopper 270 may perform a frequency demodulation on the current $I_o$ having a frequency component that has been converted by the second chopper 230.

In one example, when a control signal (not shown) used to control a first chopper 220, the second chopper 230, or the third chopper 270 remains in a logic state High or a logic state Low, an input signal of a chopper controlled by the control signal is directly output without the frequency conversion being performed on the input signal. When the control signal used to control the first chopper 220, the second chopper 230, or the third chopper 270 is repetitively changed between the logic state High and the logic state Low as time elapses, the input signal of the chopper is output after the frequency conversion is performed on the input signal.

In another example, the signal processing apparatus 200 may also include an element to decrease an output impedance of the signal processing apparatus 200. For example, the signal processing apparatus 200 may also include a buffer (not shown) connected to the output terminals of the signal processing apparatus 200 to decrease the output impedance.

In the current measuring mode, the signal processing apparatus 200 operates as described below.

Referring to FIG. 3, when the signal processing apparatus 200 operates in the current measuring mode, the signal processing apparatus 200 controls an input voltage input to the signal processing apparatus 100 to not be processed. The signal processing apparatus 200 controls the switches SW_$V_{ip}$ 232 and SW_$V_{in}$ 234 that are used to connect inputs of the input element 240 to the input voltages $V_{ip}$ and $V_{in}$ in the voltage measuring mode so that the inputs of the input element 240 are connected to reference voltages $V_{ip\_b}$ and $V_{in\_b}$ in the current measuring mode. The reference voltages $V_{ip\_b}$ and $V_{in\_b}$ may have the same voltage level as each other or different voltage levels from each another. Also, the reference voltages $V_{ip\_b}$ and $V_{in\_b}$ may have a fixed voltage level or a variable voltage level as time elapses.

When the input currents $I_{ip}$ and $I_{in}$ need to be amplified by a relatively high amplification level, the signal processing apparatus 200 controls the switch SW_$I_{ip}$ 252 controlling the flow of the input current $I_{ip}$ and the switch SW_$I_{in}$ 254 controlling the flow of the input current $I_{in}$ to be closed to allow the input currents $I_{in}$ and $I_{ip}$ to flow through the input resistor 250, for example, $R_i$. Also, the signal processing apparatus 200 controls switches SW_$I_{op}$ 256 and SW_$I_{on}$ 258 to be opened to prevent the input currents $I_{in}$ and $I_{ip}$ from flowing through the output resistor 280, for example, $R_o$.

When the input currents $I_{ip}$ and $I_{in}$ need to be amplified by a relatively low level, the signal processing apparatus 200 controls the switches SW_$I_{ip}$ 252 and SW_$I_{in}$ 254 connected to opposite ends of the input resistor 250 to be opened to prevent the input currents $I_{in}$ and $I_{ip}$ from flowing through the input resistor 250, and controls the switches SW_$I_{op}$ 256 and SW_$I_{on}$ 258 connected to opposite ends of the output resistor 280 to be closed to allow the input currents $I_{in}$ and $I_{ip}$ to flow through the output resistor 280.

In one example, when the input current to be measured exceeds an operational range of the signal processing circuit 200, the signal processing apparatus 200 may control a level of the current flowing in the signal processing apparatus 200 to be within the operational range using an input current compensator 210. For example, when an input current to be measured includes a direct current (DC) current of 100 microamperes (μA) and an alternating current (AC) current of 1 μA, and a maximum level of current allowed to flow through the input resistor 250 is 10 μA, the input current compensator 210 outputs a compensation current to flow in the circuit to offset the DC current of 100 μA. Due to the compensation current output by the input current compensator 210, only the AC current of 1 μA flows through the input resistor 250.

To minimize noise flowing into the signal processing apparatus 200 in a process of amplifying the input current to be measured, the signal processing apparatus 200 may modulate the frequency component of the input current using the first chopper 220, and demodulate the frequency component using the third chopper 270. Alternatively, in response to a modulated frequency component of the input current to be measured, the signal processing apparatus 200 may demodulate a modulated signal using the third chopper 270.

Figure 4:
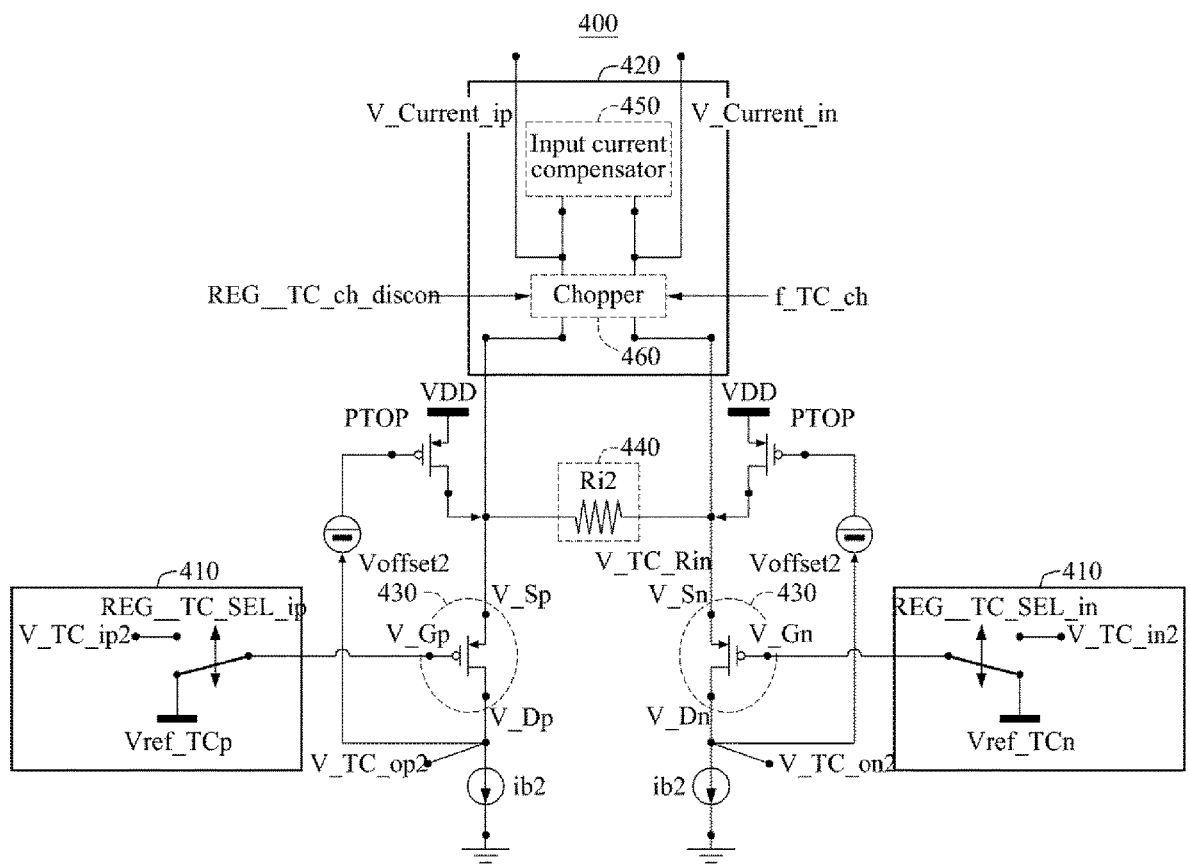
FIG. 4 is a diagram illustrating another example of a circuit for implementing a signal processing apparatus.

FIG. 4 is a diagram illustrating another example of a circuit for implementing a signal processing apparatus 400.

Referring to FIG. 4, the signal processing apparatus 400 includes an input voltage selector 410, an input current controller 420, an input element 430, and a load element 440. The signal processing apparatus 400 is operable in a voltage measuring mode and a current measuring mode. In one example, the signal processing apparatus 400 corresponds to a transconductance stage of an IA.

The input voltage selector 410 selects an input voltage from a plurality of input voltages. In the example in FIG. 4, the plurality of input voltages include a target voltage to be measured and a preset reference voltage. For example, a biosignal such as an ECG may be input as the target voltage to be measured. In FIG. 4, voltages V_TC_ip2 and V_TC_in2 are the target voltage to be measured, and voltages Vref_TCp and Vref_TCn are the preset reference voltage. The voltages Vref_TCp and Vref_TCn may have the same voltage level as each other or different voltage levels from each another. Also, the voltages Vref_TCp and Vref_TCn may have a fixed voltage level or a variable voltage level as time elapses.

The input voltage selector 410 is connected to the input element 430. In the example in FIG. 4, the input element 430 is a transistor having a gate connected to the input voltage selector 410, but is not limited thereto. The input voltage selector 410 selects an input voltage to be applied to the input element 430 using a switch. The input element 430 generates a current in response to the input voltage selected by the input voltage selector 410 in the voltage measuring mode, and thus is a transconductance element. For example, the input element 430 may be a transistor and include a plurality of transconductance elements. Thus, the input element 430 converts the input voltage to be measured into a current. The input voltage to be applied to the input element 430 is determined by a control signal. In FIG. 4, REG_TC_SEL_ip and REG_TC_SEL_in are control signals that control the switching operation performed by the input voltage selector 410. A source of the input element 430 is connected to a drain of a transistor PTOP, which forms a cascode circuit with the input element 430. A drain of the input element 430 is biased by a constant-current source providing a fixed current ib2. A source of the transistor PTOP is connected to a power supply voltage VDD. A gate of the transistor PTOP is biased by a voltage Voffset2.

The input current controller 420 controls an inflow of an input current in conjunction with an operation of the input voltage selector 410. For example, the input current controller 420 blocks the inflow of the input current when an input voltage input to the signal processing apparatus 400 is the target voltage to be measured by the input voltage selector 410. The input current to be measured is input to the signal processing apparatus 400 by the input current controller 420. For example, a biosignal such as a PPG may be input to the signal processing apparatus 400 as the input current. The input current controller 420 controls the inflow of the input current using a switch controlled by the control signal. The input current controller 420 allows the input current to flow into the signal processing apparatus 400 or block the inflow of the input current based on a measurement mode. In FIG. 4, V_Current_ip and V_Current_in are the input current to be measured, and REG_TC_ch_discon is the control signal controlling the switching operation of the input current controller 420.

The load element 440 is functionally connected to the input current controller 420 and the input element 430. For example, output terminals of the input current controller 420 are connected to opposite ends of the load element 440, and one end of the input element 430 is connected to the load element 440. In this example, "being functionally connected" includes "being directly connected to the input current controller 420 and the input element 430" and "being affected by the input current controller 420 and the input element 430". For example, the load element 440 may be a resistor having a resistance Ri2. A current flowing through the ends of the load element 440 may be changed due to the current flowing through the input element 430 or the input current flowing through the input current controller 420.

In another example, the input current controller 420 may also include an input current compensator 450 to adjust a level of the input current. The input current compensator 450 generates a compensation current to adjust the level of the input current. When a level of an input current to be measured exceeds an operational range of the signal processing apparatus 400, the input current compensator 450 a compensation current to offset the level of the input current to be within the operational range of the signal processing apparatus 400.

For example, the input current compensator 450 outputs the compensation current to decrease a DC level of the input current to be within a preset range. To decrease the DC level of the input current, the input current compensator 450 outputs a compensation current having a negative DC level, for example, −3 milliamperes (mA). The level of the input current is adjusted by adding the input current flowing into the signal processing apparatus 400 and the compensation current output by the input current compensator 450.

The input current compensator 450 may operate in a manual adjustment mode and an automatic adjustment mode. For example, in the manual adjustment mode, the input current compensator 450 manually adjusts the level of the input current under a control of a user. In the automatic adjustment mode, the input current compensator 450 adaptively adjusts the level of the input current based on an output signal of the signal processing apparatus 400. For example, in the automatic adjustment mode, the input current compensator 450 may extract a signal of a low-frequency band from the output signal of the signal processing apparatus 400, and determine whether the level of the input current is to be adjusted based on a level of the extracted signal of the low-frequency band. Based on a result of the determining, the input current compensator 450 determines a level of the compensation current to be used to adjust the level of the input current, and adjusts the level of the input current flowing in the signal processing apparatus 400 by outputting the compensation current having the determined level.

In the automatic adjustment mode, the signal processing apparatus 400 may also include an input current compensation controller (not shown) to generate a control signal used to control the input current compensator 450. The input current compensation controller controls the level of the compensation current output by the input current compensator 450 based on the output signal of the signal processing apparatus 400. In one example, the signal processing apparatus 400 includes a low-pass filter (not shown) to output the signal of the low-frequency band from the output signal of the signal processing apparatus 400, and a comparator (not shown) to compare a level of an output signal of the low-pass filter to a level of a preset reference signal and output a result of the comparing to the input current compensation controller. The input current compensation controller generates the control signal to control the input current compensator 450 based on the result of the comparing. A detailed explanation of the input current compensation controller will be provided with reference to FIG. 12.

In another example, the input current controller 420 also includes a chopper 460 to modulate a frequency component of the input current based on a control signal. The chopper 460 changes connections between input ends and output ends of the input current controller 420 based on the control signal. Low-frequency noise, 1/f noise, or flicker noise may be reduced when the chopper 460 performs the modulation on the frequency component of the input current. For example, the low-frequency noise occurring in the signal of the low-frequency band may be reduced when the input current is modulated into a signal of a high-frequency band by the chopper 460. When the chopper 460 does not perform the above modulation, the chopper 460 operates as a switch to allow and block the inflow of the input current.

Hereinafter, the signal processing apparatus 400 operating in the voltage measuring mode and the signal processing apparatus 400 operating in the current measuring mode will be described.

In the voltage measuring mode, the signal processing apparatus 400 operates as described below.

In the voltage measuring mode, the signal apparatus 400 blocks the inflow of the input current and selects a voltage to be measured as the input voltage.

The input voltage selector 410 applies an input voltage to be measured to the input element 430. For example, the input current selector 410 applies an input voltage V_TC_ip2 to be measured to a gate node V_Gp of one input element 430, and applies an input voltage V_TC_in2 to be measured to a gate node V_Gn of the other input element 430. The input voltage V_TC_ip2 and the input voltage V_TC_in2 have a differential input relationship. When control signals REG_TC_SEL_ip and REG_TC_SEL_in have a logically high value, for example, H, the input voltage V_TC_ip2 is applied to the gate node V_Gp and the input voltage V_TC_in2 is applied to the gate node V_Gn so that the input voltage to be measured is input to the signal processing apparatus 400.

Due to the input voltages V_TC_ip2 and V_TC_in2 having the differential input relationship, the current flowing through the ends of the load element 440 may be changed.

In response to the applied input voltage, one input element 430 generates a current flowing from a source node V_Sp to a drain node V_Dp, and another input element 430 generates a current flowing from a source node V_Sn to a drain node V_Dn. The drain node V_Dp is connected to an output node V_TC_op2 of the signal processing apparatus 400, and the drain node V_Dn is connected to an output node V_TC_on2 of the signal processing apparatus 400.

The input current controller 420 blocks the inflow of the input current into the signal processing apparatus 400 in the voltage measuring mode. For example, when a control signal REG_TC_ch_discon has a logically high value, switches (not shown) included in the chopper 460 of the input current controller 420 are opened so that the input current does not flow into the ends of the load element 440.

In the current measuring mode, the signal processing apparatus 400 operates as described below.

In the current measuring mode, the signal processing apparatus 400 allows the inflow of the input current to be measured into the signal processing apparatus 400, and selects the preset reference voltage as the input voltage in lieu of the voltage to be measured.

The input voltage selector 410 applies a reference voltage having a fixed voltage level to the input element 430. For example, when the control signal REG_TC_SEL_in has a logically low value, for example, L, the input voltage selector 410 applies a reference voltage Vref_TCp having the fixed voltage level to the gate node V_Gp of one input element 430, and applies a reference voltage Vref_TCn having the fixed voltage level to the gate node V_Gn of the other input element 430.

Since a fixed current ib2 flows through each of the input elements 430, a constant voltage level may be maintained at each of the source nodes V_Sp and V_Sn of the input elements 430. By adjusting a level of the reference voltage Vref_TCp, a voltage having a desired level may be provided to the source node V_Sp, and by adjusting a level of the reference voltage Vref_TCn, a voltage having a desired level may be provided to the source node V_Sn.

The input current controller 420 allows the inflow of the input current to be measured into the signal processing apparatus 400. For example, the input current controller 420 allows an inflow of input currents V_Current_ip and V_Current_in to be measured. The input current V_Current_ip and the input current V_Current_in may have a differential input relationship. When the control signal REG_TC_ch_discon has a logically low value, the switches included in the chopper 460 are connected so that the input end and the output end are connected in the chopper 460.

Due to the input currents V_TC_ip2 and V_TC_in2 having the differential input relationship, the current flowing through the ends of the load element 440 may be changed.

Based on the control signal REG_TC_ch_discon, the chopper 460 may operate as a switch connecting the input end of the chopper 460 with the output end of the chopper 460 and modulate the frequency component of the input current through a periodic switching operation.

In another example, the input current controller 420 may also include the input current compensator 450 to adjust a level of the input current. When the level of the input current to be measured is beyond an operational range of the signal processing apparatus 400, the input current compensator 450 outputs a compensation current to offset the level of the input current to be within the operational range of the signal processing apparatus 400. Based on the compensation current, the input current is changed into a signal having a current level that can be handled by elements of the signal processing apparatus 400.

Figure 5:
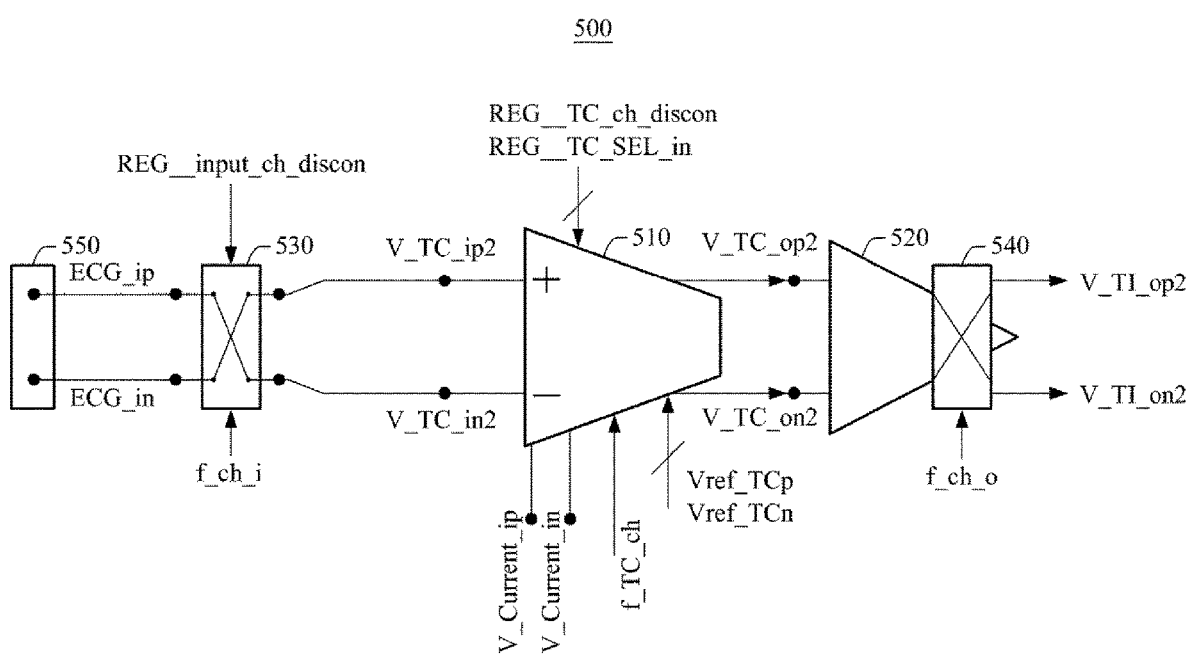
FIG. 5 is a diagram illustrating an example of a signal processing apparatus operating in a voltage measuring mode.

FIG. 5 is a diagram illustrating an example of a signal processing apparatus 500 operating in a voltage measuring mode.

Referring to FIG. 5, the signal processing apparatus 500 includes a transconductance stage 510 and a transimpedance stage 520. The transconductance stage 510 corresponds to the signal processing apparatus 400 of FIG. 4. The transconductance stage 510 may operate in either the voltage measuring mode or a current measuring mode. The transconductance stage 510 controls an inflow of an input current and selects a type of an input voltage to be applied based on a measuring mode.

In FIG. 5, the signal processing apparatus 500 measures an ECG in the voltage measuring mode. ECG_ip and ECG_in are ECG signals measured by a sensor 550 such as a bioelectrode. In the voltage measuring mode, the transconductance stage 510 selects a voltage to be measured as an input voltage and blocks the inflow of the input current. For example, in the voltage measuring mode, the transconductance stage 510 selects input voltages V_TC_ip2 and V_TC_in2 to be measured to be applied to an internal input element, and block inflows of input currents V_Current_ip and V_Current_in. The transconductance stage 510 selects the type of the input voltage based on a control signal REG_TC_SEL_in. The transconductance stage 510 controls a switch used to determine whether the input current is allowed to flow based on a control signal REG_TC_ch_discon.

The transimpedance stage 520 generates output voltages V_TI_op2 and V_TI_on2 based on a current output from the transconductance stage 510. The transimpedance stage 520 may include a current mirror circuit.

The signal processing apparatus 500 may also include an input chopper 530 to modulate a frequency component of the input voltage of the transconductance stage 510 in the voltage measuring mode. The input chopper 530 modulates the input voltage into a signal of a high-frequency band, thereby reducing low-frequency noise. A control signal REG_input_ch_discon determines whether the input chopper 530 operates. A control signal f_ch_i controls a connection of each switch included in the input chopper 530.

The transimpedance stage 520 includes an output chopper 540 to demodulate into a signal of a low-frequency band the input signal that has been modulated into the signal of the high-frequency band by the input chopper 530. A control signal f_ch_o controls a connection of each switch included in the output chopper 540. In one example, the control signal f_ch_o applied to the output chopper 540 has the same signal waveform as the control signal f_ch_i applied to the input chopper 530.

Figure 6A:
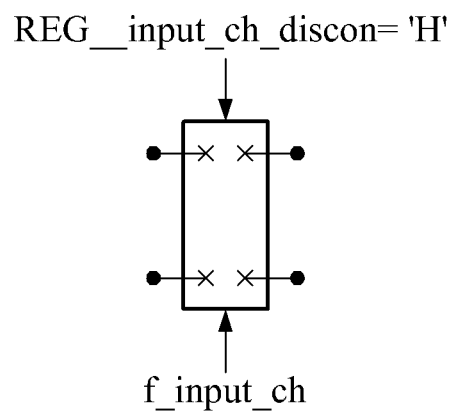
FIGS. 6A and 6B are diagrams illustrating examples of operating an input chopper based on a control signal.
Figure 6B:
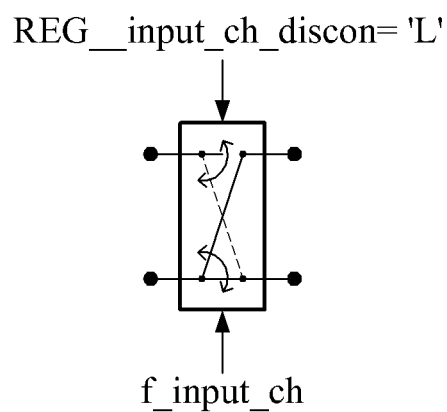

FIGS. 6A and 6B are diagrams illustrating examples of operating an input chopper based on a control signal.

The control signal REG_input_ch_discon determines whether the input chopper operates. For example, when the control signal REG_input_ch_discon is in a logically high state H as shown in FIG. 6A, all switches included in the input chopper are turned off so that a connection between an input end and an output end of the input chopper is blocked. Conversely, the input chopper operates when the control signal REG_input_ch_discon is in a logically low state L as shown in FIG. 6B. When the input chopper operates, operations of the switches included in the input chopper are controlled based on a control signal f_input_ch. A control signal f_input_ch_bar (not shown) that is an inverse waveform of the control signal f_input_ch may be generated based on the control signal f_input_ch. Connections among the switches included in the input chopper may be changed based on the control signal f_input_ch and the control signal f_input_ch_bar.

Figure 7A:
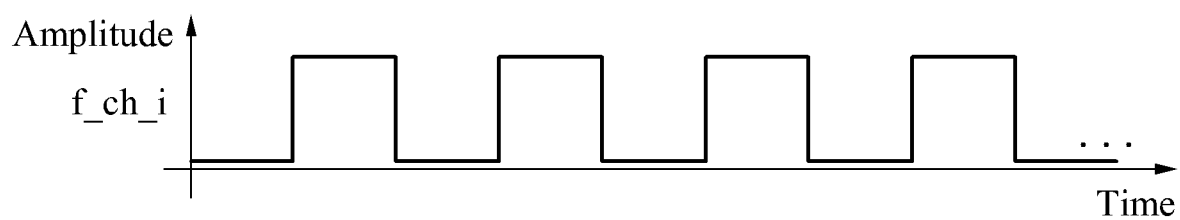
FIGS. 7A through 7C are diagrams illustrating examples of a control signal input for each chopper in a voltage measuring mode.
Figure 7B:
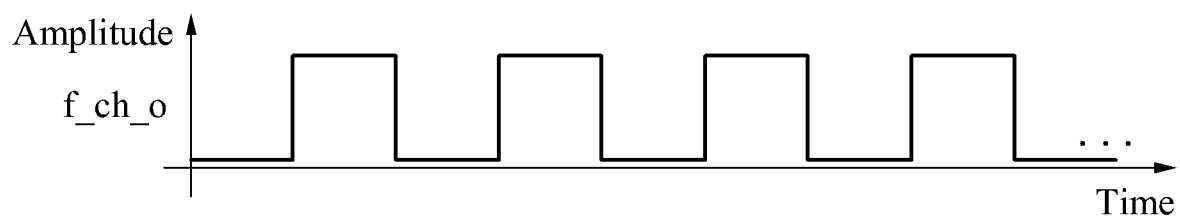
Figure 7C:
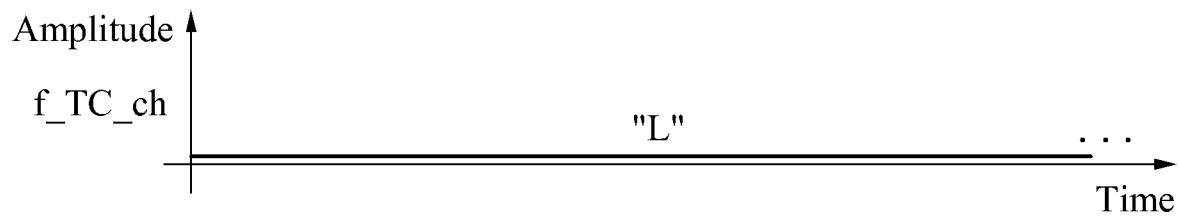

FIGS. 7A through 7C are diagrams illustrating examples of a control signal input for each chopper in a voltage measuring mode.

An example of a control signal f_ch_i applied to an input chopper is illustrated in FIG. 7A. An example of a control signal f_ch_o applied to an output chopper is illustrated in FIG. 7B. An example of a control signal f_TC_ch applied to a chopper included in an input current controller is illustrated in FIG. 7C. In the voltage measuring mode, an input voltage is modulated into a signal of a high-frequency band by the input chopper, and the modulated input voltage is demodulated into a signal of a low-frequency band by the output chopper. In the voltage measuring mode, connections of switches included in the chopper of the input current controller are blocked, so the control signal f_TC_ch is in a logically low state.

Figure 8:
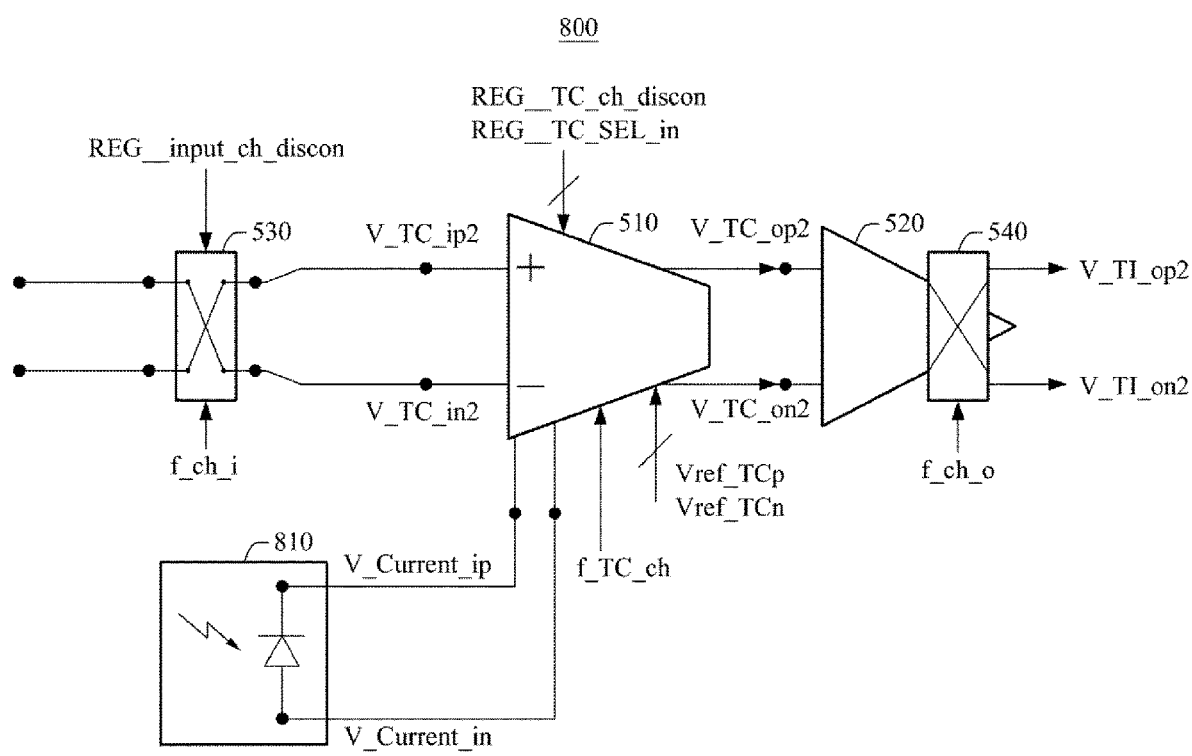
FIGS. 8 and 9 are diagrams illustrating examples of a signal processing apparatus operating in a current measuring mode.
Figure 9:
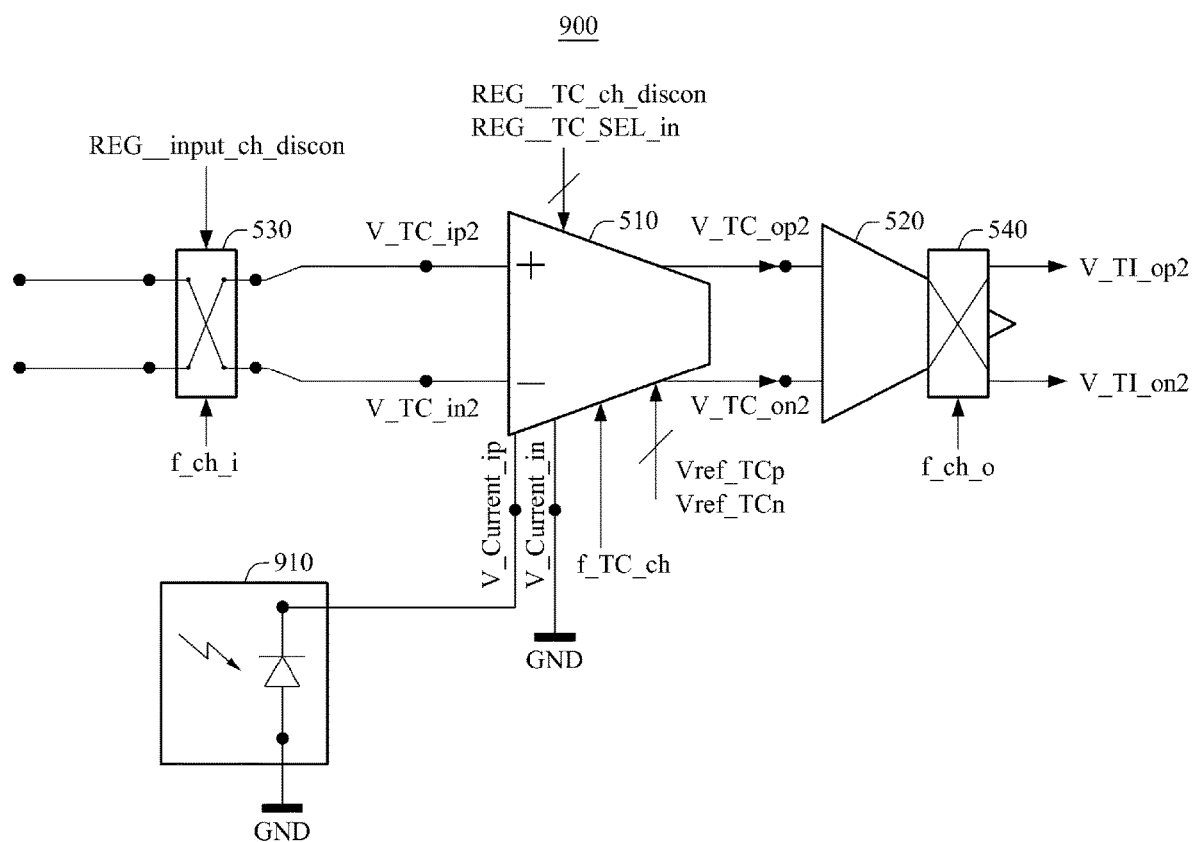

FIG. 8 is a diagram illustrating an example of a signal processing apparatus 800 operating in a current measuring mode. FIG. 9 is a diagram illustrating an example of a signal processing apparatus 900 operating in a current measuring mode.

In FIG. 8, the signal processing apparatus 800 measures a photovoltaic mode PPG in the current measuring mode. Currents V_Current_ip and V_Current_in output from a light detector 810 of FIG. 8 are input to the transconductance stage 510.

In FIG. 9, the signal processing apparatus 900 measures a photoconductive mode PPG in the current measuring mode. A current V_Current_ip output from a light detector 910 of FIG. 9 is input to the transconductance stage 510.

Referring to FIGS. 8 and 9, in the current measuring mode, the transconductance stage 510 applies reference voltages Vref_TCp and Vref_TCn, each preset as an input voltage, to internal input elements of the transconductance stage 510. Based on a control signal REG_TC_SEL_in, the input voltage applied to an input element is determined and input voltages V_TC_in2 and V_TC_ip2 input to the transconductance stage 510 may be blocked. A control signal REG_TC_ch_discon is used to determine whether an input current is allowed to flow into the transconductance stage 510. A control signal f_TC_ch is used to control a chopper included in the transconductance stage 510. Through switching operations of switches included in the chopper, the input current may be modulated into a signal of a high-frequency band.

The transimpedance stage 520 includes the output chopper 540 to demodulate into a low-frequency band an input signal that has been modulated into the signal of the high-frequency band by the chopper included in the transconductance stage 510. A control signal f_ch_o is used to control a connection of each switch included in the output chopper 540. In one example, the control signal f_ch_o applied to the output chopper 540 has the same waveform as a control signal f_TC_ch applied to the chopper of the transconductance stage 510.

FIGS. 10A through 11C are diagrams illustrating examples of a control signal input for each chopper in a current measuring mode.

Figure 10A:
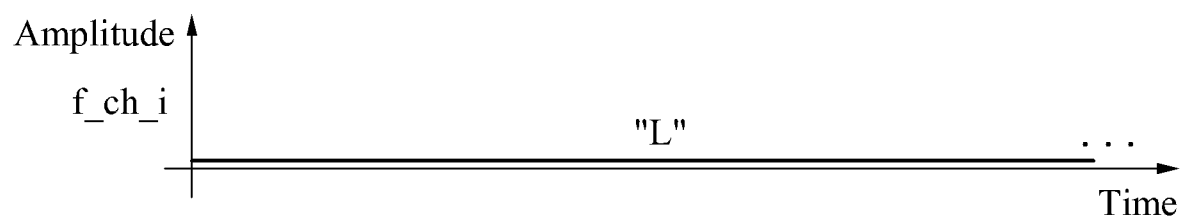
FIGS. 10A through 11C are diagrams illustrating examples of a control signal input for each chopper in a current measuring mode.
Figure 10B:
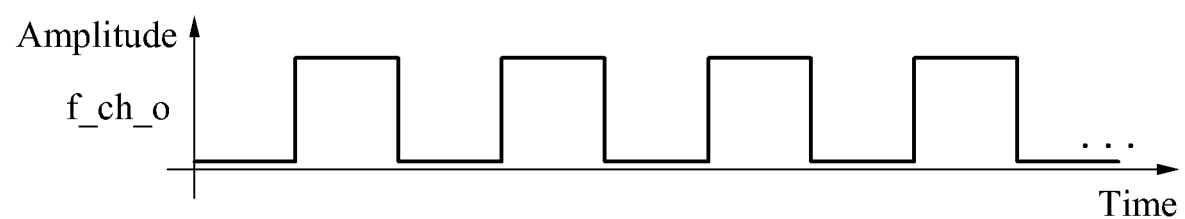
Figure 10C:
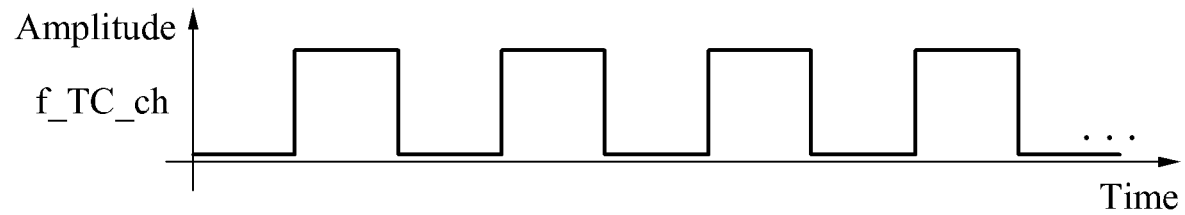

Examples of a control signal applied to each chopper when the chopper is operated in the current measuring mode are illustrated in FIGS. 10A through 10C.

An example of control signal f_ch_i applied to an input chopper is shown in FIG. 10A. An example of control signal f_ch_o applied to an output chopper is shown in FIG. 10B. An example of a control signal f_TC_ch applied to a chopper included in a transconductance stage is shown in FIG. 10C. In the current measuring mode, an input current is modulated into a signal of a high-frequency band by the chopper of the transconductance stage, and the modulated input current is demodulated into a signal of a low-frequency band by the output chopper. In a current measuring mode, the input chopper is not used, so the control signal f_ch_i is in a logically low state.

In one example, when the control signal f_TC_ch is in a logically high state, a first input end is connected to a first output end and a second input end is connected to a second output end in the chopper included in the transconductance stage, and when the control signal f_TC_ch is in the logically low state, the first input end is connected to the second output end and the second input end is connected to the first output end in the chopper included in the transconductance stage.

Figure 11A:
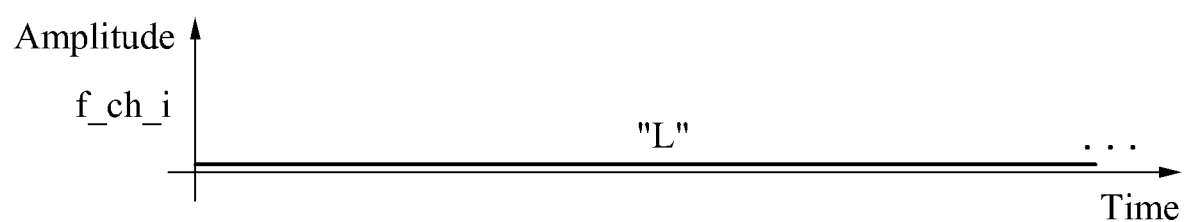
Figure 11B:
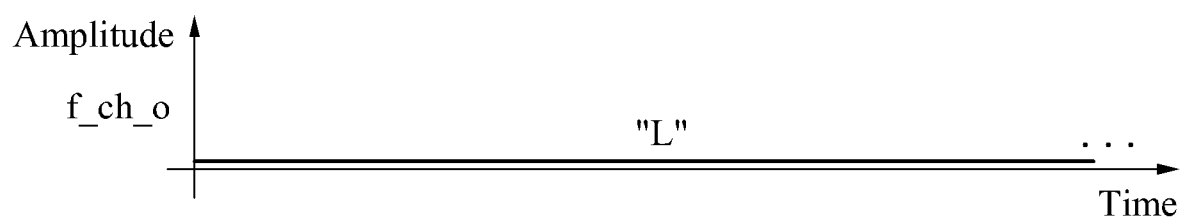
Figure 11C:
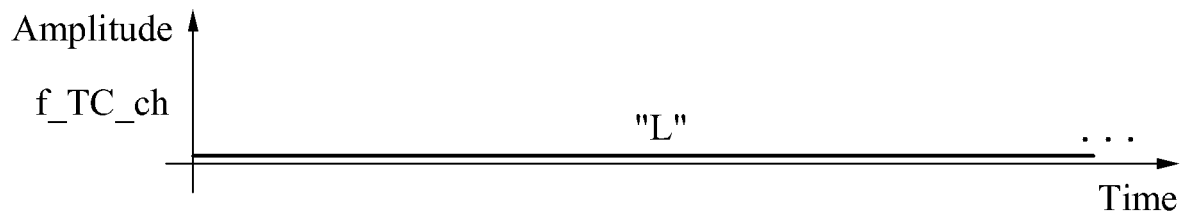

Examples of a control signal applied to each chopper when the chopper is not operated in the current measuring mode are illustrated in FIGS. 11A through 11C.

An example of a control signal f_ch_i applied to an input chopper is shown in FIG. 11A. An example of a control signal f_ch_o applied to an output chopper is shown in FIG. 11B. An example of a control signal f_TC_ch applied to a chopper included in a transconductance stage is shown in FIG. 11C. In one example, when the chopper is not operated, each of the control signal f_ch_i, the control signal f_ch_o, and the control signal f_TC_ch are in a logically low state.

Figure 12:
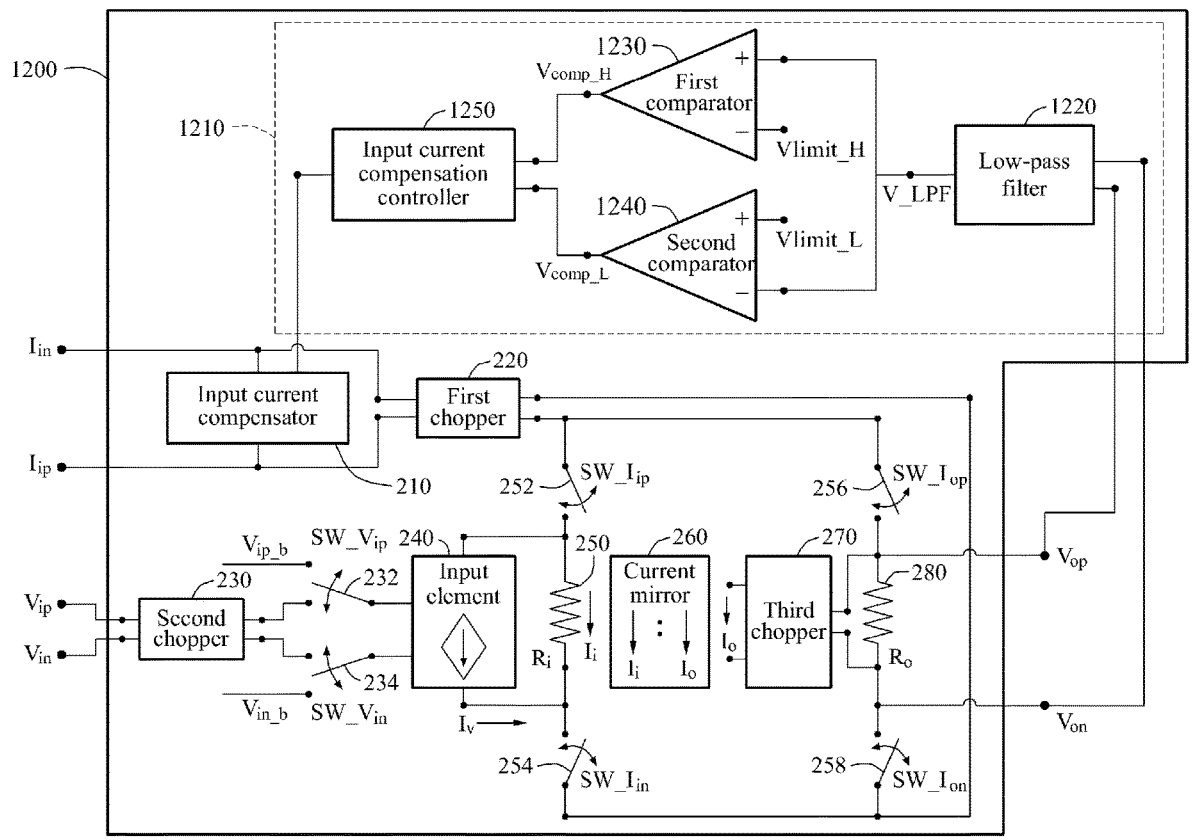
FIG. 12 is a diagram illustrating an example of an operation performed by a signal processing apparatus in an automatic adjustment mode for adjusting an input current level.

FIG. 12 is a diagram illustrating an example of an operation performed by a signal processing apparatus 1200 in an automatic adjustment mode for adjusting an input current level.

Referring to FIG. 12, the signal processing apparatus 1200 includes the input current compensator 210 to adjust the input current level in a current measuring mode. In one example, the signal processing apparatus 1200 also includes a control circuit 1210 to control the input current compensator 210 based on an output signal of the signal processing apparatus 1200. The control circuit 1210 includes an input current compensation controller 1250, a low-pass filter 1220, a first comparator 1230, and a second comparator 1240.

In one example, an output end of the signal processing apparatus 1200 is connected to an input end of the low-pass filter 1220, and an output end of the low-pass filter 1220 is connected to an input end of each of the first comparator 1230 and the second comparator 1240. An output end of each of the first comparator 1230 and the second comparator 1240 is connected to an input end of the input current compensation controller 1250, and an output end of the input current compensation controller 1250 is connected to the input current compensator 210.

The low-pass filter 1220 extracts a signal of a low-frequency band from output signals $V_{op}$ and $V_{on}$ of the signal processing apparatus 1200. For example, the signal processing apparatus 1200 may extract a signal of a frequency band less than or equal to 0.1 hertz (Hz) from the output signal of the signal processing apparatus 1200 using the low-pass filter 1220. A signal V_LPF of the low-frequency band output from the low-pass filter 1220 is input to the first comparator 1230 and the second comparator 1240.

The first comparator 1230 compares the signal V_LPF of the low-frequency band to a control signal Vlimit_H, and outputs a signal $V_{comp\_H}$ indicating a result of the comparing. The second comparator 1240 compares the signal V_LPF of the low-frequency band to a control signal Vlimit_L, and outputs a signal $V_{comp\_L}$ indicating a result of the comparing. An upper limit of a voltage range of the extracted signal of the low-frequency band is set by the control signal Vlimit_H, and a lower limit of the voltage range of the extracted signal of the low-frequency band is set by the control signal Vlimit_L.

In one example, when the signal V_LPF output from the low-pass filter 1220 is in a range between the control signal Vlimit_L and the control signal Vlimit_H, for example, Vlimit_L<V_LPF<Vlimit_H, the signal $V_{comp\_H}$ output from the first comparator 1230 and the signal $V_{comp\_L}$ output from the second comparator 1240 have a logically low value. In this example, the control signal output from the input current compensation controller 1250 to the input current compensator 210 remains the same as a previous control signal output from the input current compensation controller 1250.

In another example, when a level of the signal V_LPF output from the low-pass filter 1220 is greater than a level of the control signal Vlimit_H, the first comparator 1230 outputs a logically high value, and the second comparator 1240 outputs a logically low value. In this example, the input current compensation controller 1250 outputs, to the input current compensator 210, a control signal to decrease the level of the signal V_LPF.

In another example, when the level of the signal V_LPF output from the low-pass filter 1220 is less than the level of the control signal Vlimit_L, the first comparator 1230 outputs a logically low value and the second comparator 1240 outputs a logically high value. In this example, the input current compensation controller 1250 outputs, to the input current compensator 210, a control signal to increase the level of the signal V_LPF.

As described above, the input current compensation controller 1250 automatically controls a level of a compensation current output by the input current compensator 210 based on an output signal of the signal processing apparatus 1200. Other operations of the signal processing apparatus 1200 of FIG. 12 were previously explained with reference to FIGS. 2 and 3.

Figure 13:
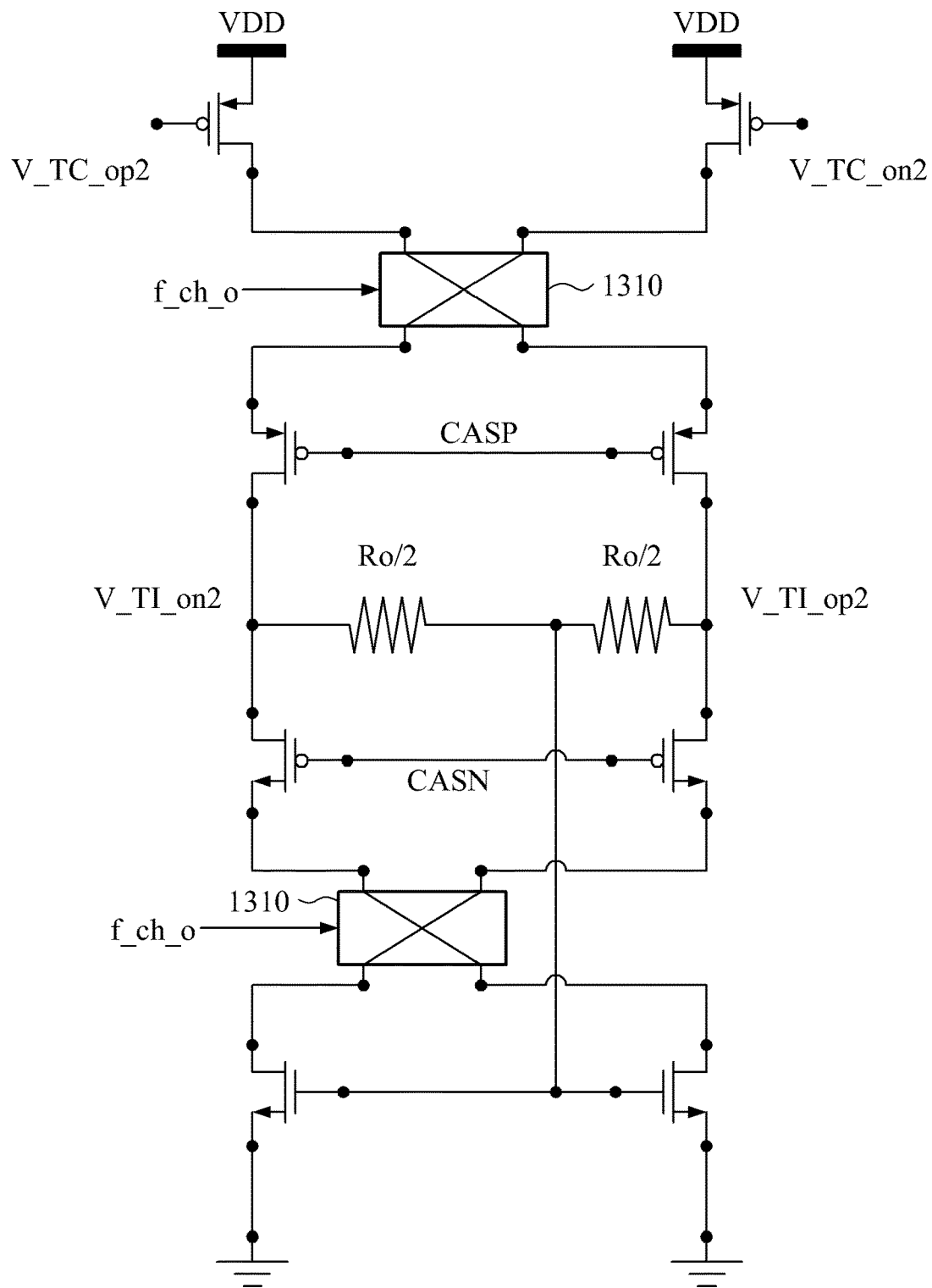
FIG. 13 is a diagram illustrating an example of a configuration of a transimpedance stage.

FIG. 13 is a diagram illustrating an example of a configuration of a transimpedance stage 1300.

Figure 14:
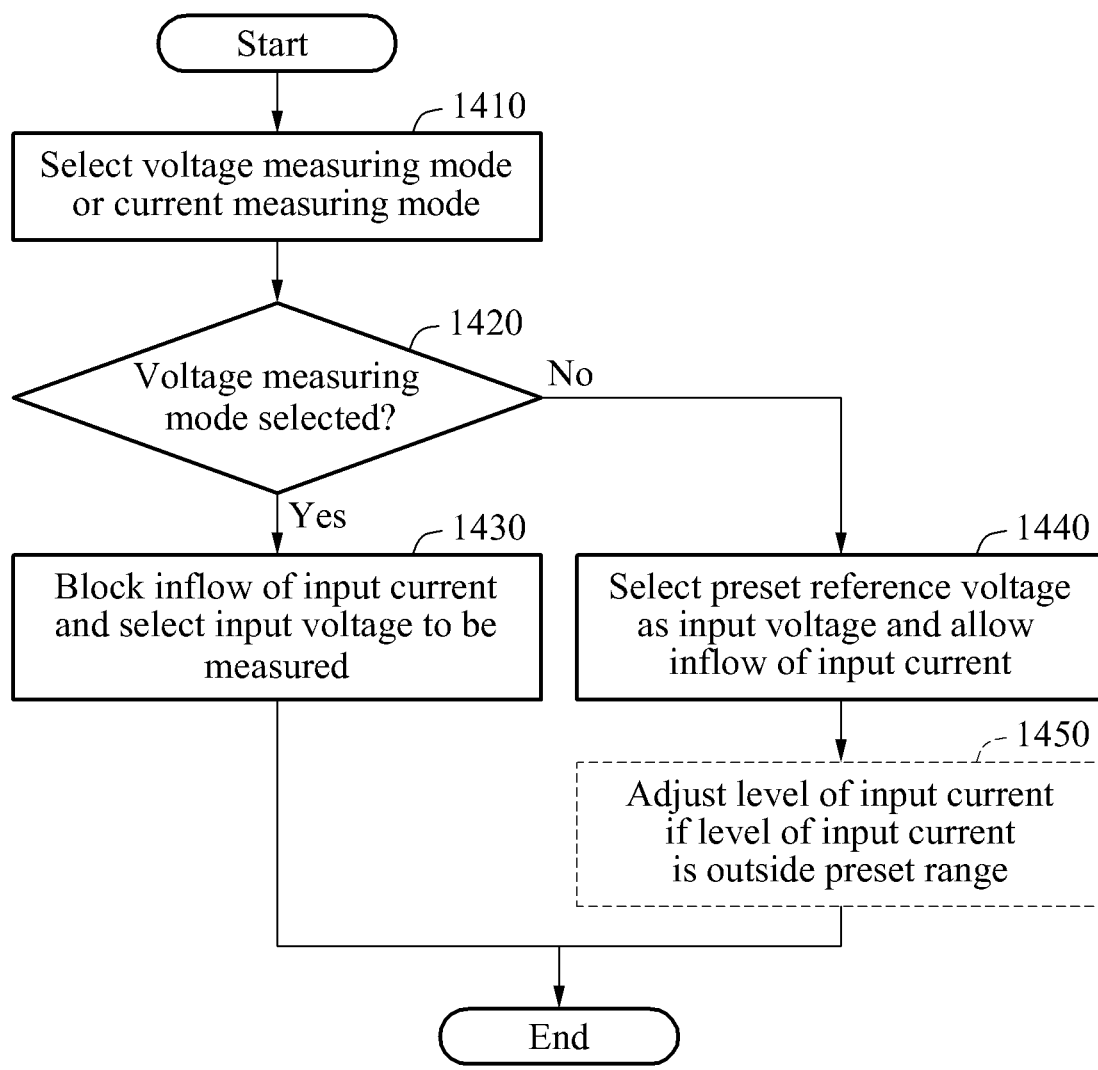
FIG. 14 is a flowchart illustrating an example of a signal processing method.

The transimpedance stage 1300 generates output voltages V_TI_op2 and V_TI_on2 based on a current output from a transconductance stage. The transimpedance stage 1300 includes a current mirror circuit constituted by all of the elements in FIG. 13 except for the two transistors at the top that receive V_TC_op2 and V_TC_on2 and the output choppers 1310. The transimpedance stage 1300 includes the output choppers 1310 to demodulate into a signal of a low-frequency band an input signal that has been modulated into a signal of a high-frequency band by an input chopper or a chopper included in the transconductance stage. The two output choppers 1310 enable the input signal to be demodulated more accurately through two frequency demodulation processes. In FIG. 14, VDD denotes a power supply voltage, CASP denotes PMOS cascode transistors, Ro denotes an output resistance, and CASN denotes NMOS cascode transistors.

FIG. 14 is a flowchart illustrating an example of a signal processing method.

In operation 1410, a signal processing apparatus selects a voltage measuring mode and a current measuring mode. The signal processing apparatus controls an inflow of an input current or selects a type of an input voltage to be applied to an input element based on the selected measuring mode.

In operation 1420, the signal processing apparatus determines whether the voltage measuring mode or the current measuring mode has been selected.

When it is determined in operation 1420 that the voltage measuring mode has been selected, the signal processing apparatus blocks the inflow of the input current and selects an input voltage to be measured in operation 1430. The signal processing apparatus applies the input voltage to be measured to an input element, and blocks the inflow of the input current by turning off a switch used to control the inflow of the input current.

When it is determined in operation 1420 that the current measuring mode has been selected, the signal processing apparatus selects a preset reference voltage and allows the inflow of the input current in operation 1440. The signal processing apparatus applies the preset reference voltage, which may have a fixed voltage level, to the input element, and allows the inflow of the input current by turning on the switch used control the inflow of the input current. Also, the signal processing apparatus may modulate the input current into a signal of a high-frequency band using a chopper. The input current modulated into the signal of the high-frequency band may be demodulated into a signal of a low-frequency band by an output chopper.

In one example, the signal processing method may also include operation 1450 of adjusting a level of the input current to be within a preset range. When the level of the input current is outside an operational range of the signal processing apparatus, the signal processing apparatus may generate a compensation current and adjust the input current to a signal having an appropriate level using the compensation current. The signal processing apparatus may adjust the level of the input current in a manual adjustment mode or in an automatic adjustment mode. In the manual adjustment mode, the signal processing apparatus manually adjusts the level of the input current under the control of a user. In the automatic adjustment mode, the signal processing apparatus determines a level of the compensation current based on the output signal of the signal processing apparatus. For example, the signal processing apparatus may extract a signal of a low-frequency band from the output signal of the signal processing apparatus, and determine a sign and a level of the compensation current based on whether a level of the extracted signal is within a preset voltage range.

Figure 15:
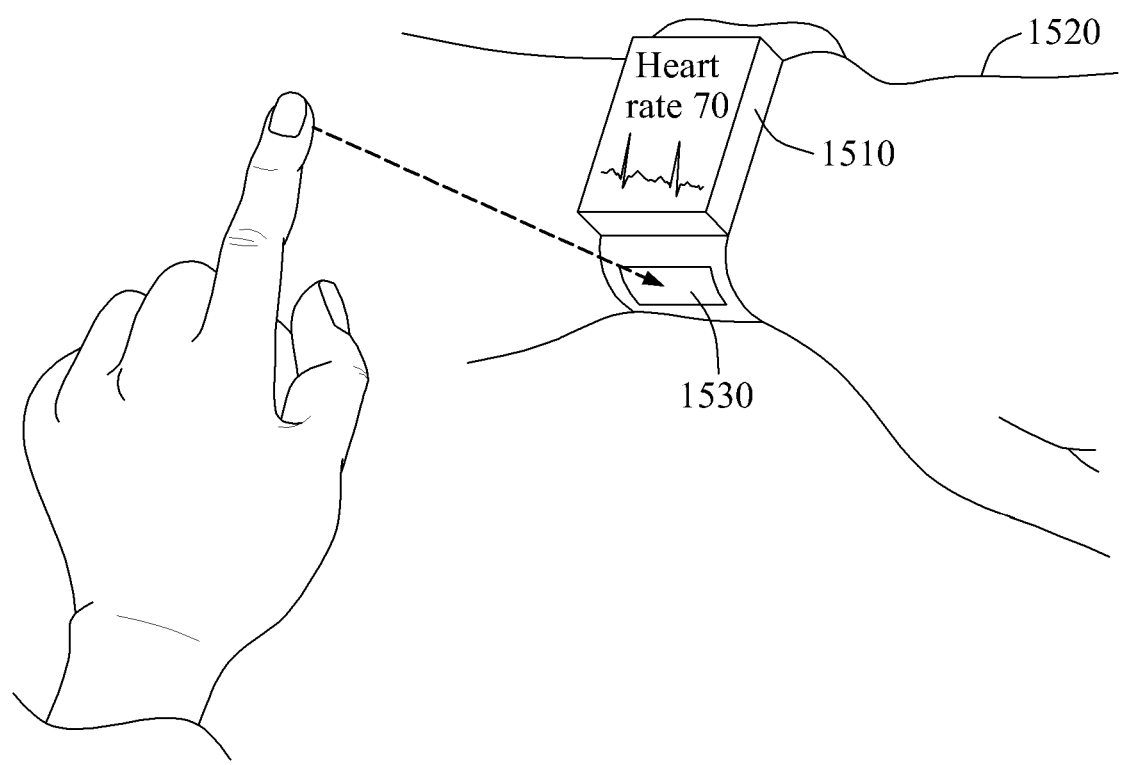
FIGS. 15 through 16B are diagrams illustrating examples of a wearable device including a signal processing apparatus.
Figure 16A:
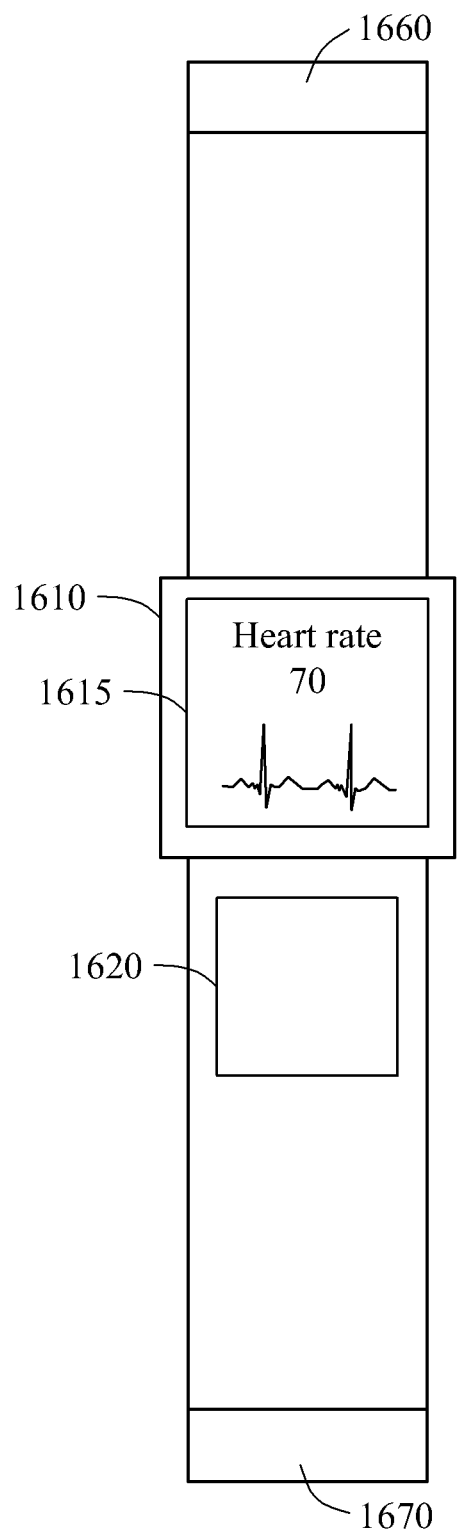
Figure 16B:
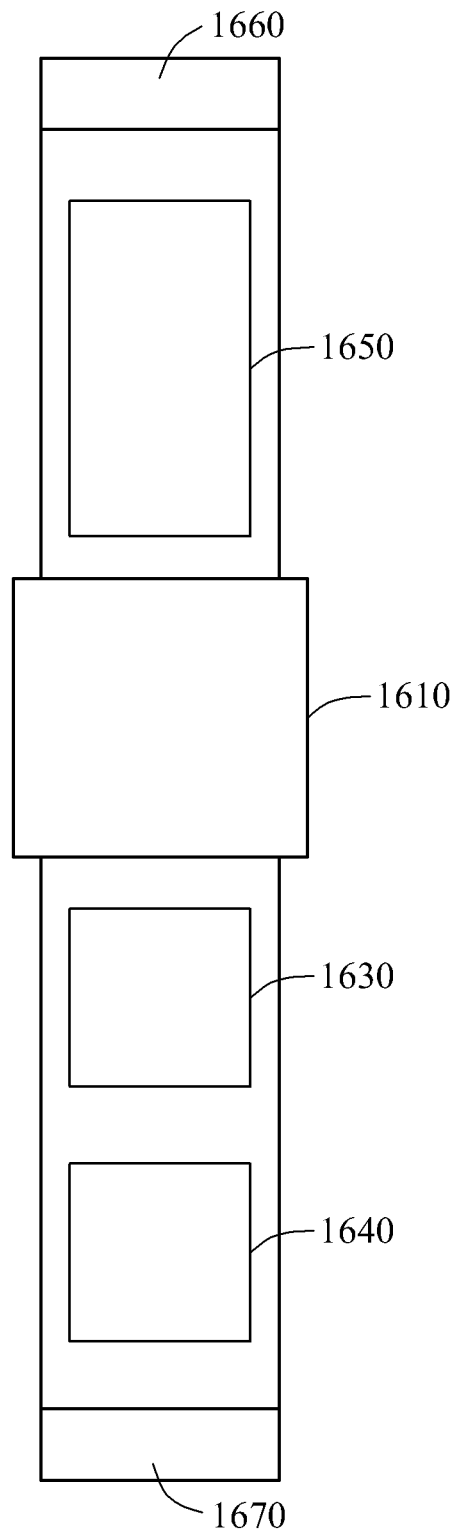

FIGS. 15 through 16B are diagrams illustrating examples of a wearable device including a signal processing apparatus.

Each signal processing apparatus described with reference to FIGS. 1 through 14 may be embedded in a wearable device 1510. In one example, the wearable device 1510 is a device to be worn on a wrist of a user provided in the form of a watch of a bracelet. The wearable device 1510 measures various biosignals from a body of a user 1520, and the measured biosignals are processed by a signal processing apparatus.

The wearable device 1510 includes various sensors for measuring a biosignal of the user 1520. For example, the wearable device 1510 includes a bioelectrode for measuring an ECG, a sensor for measuring a PPG, a sensor for measuring a heart rate of the user 1520, a sensor for measuring a body temperature, and a sensor for measuring a skin humidity.

Based on a measurement method, the biosignal may be detected as a voltage signal or a current signal, and an attribute such as a frequency bandwidth may vary in the biosignal. The signal processing apparatus processes a biosignal having a diversified attribute and converts the biosignal into a state in which the wearable device 1510 can easily analyze the biosignal. The signal processing apparatus may operate in a voltage measuring mode or in a current measuring mode. Based on a measurement mode, the signal processing apparatus controls connections between internal elements of the signal processing apparatus to analyze biosignals each having a different attribute.

The signal processing apparatus measures a current signal and a voltage signal by controlling the connection between the internal elements while sharing the internal elements. For example, in a process of measuring a voltage signal such as an ECG, the signal processing apparatus controls the connections between the internal elements to amplify the voltage signal in the voltage measuring mode. In contrast, in a process of measuring a current signal such as a PPG, the signal processing apparatus controls the connections between the internal elements to amplify the current signal in the current measuring mode.

FIG. 15 illustrates an example of the wearable device 1510 measuring the ECG from the body of the user 1520. For example, when the user 1520 is wearing the wearable device 1510 on a left wrist, and touches a sensor 1530 of the wearable device 1510 with a forefinger of a right hand, the ECG is measured from the user 1520. The sensor 1530 may be, for example, a bioelectrode for measuring the ECG. The wearable device 1510 may determine a heart rate of the user 1520, and display heart rate information and the ECG on a display.

FIGS. 16A and 16B illustrate examples of a front side and a rear side of the wearable device 1510 of FIG. 15.

Referring to FIG. 16A, the wearable device 1510 includes fasteners 1660 and 1670 to fasten the wearable device 1510 on a wrist of a user. The wearable device 1510 includes a first electrode 1620 to measure an ECG. The first electrode 1620 corresponds to the sensor 1530 of FIG. 15. Also, the wearable device 1510 includes a body 1610 including a signal processing apparatus and additional elements. The wearable device 1510 includes a display 1615 to display a measured biosignal and an analysis result of the biosignal. The display 1615 is disposed on an upper portion of the body 1610.

Referring to FIG. 16B, the wearable device 1510 includes a second electrode 1630 to measure the ECG. The second electrode 1630 is electrically isolated from the first electrode 1620, and the ECG is measured from an electrical path through the user's body between the first electrode 1620 and the second electrode 1630. The wearable device 1510 includes a reference electrode 1650 to measure a reference voltage for measuring the ECG.

Also, the wearable device 1510 includes an optical sensor 1640 to measure a current measurement-based biosignal such as a PPG and a blood oxygen saturation. The optical sensor 1640 includes a light source unit to radiate a light signal of a predetermined wavelength onto the body of the user, and a light detector to detect a biosignal based on the light signal. Hereinafter, the optical sensor 1640 will be explained in detail with reference to FIG. 17.

Figure 17:
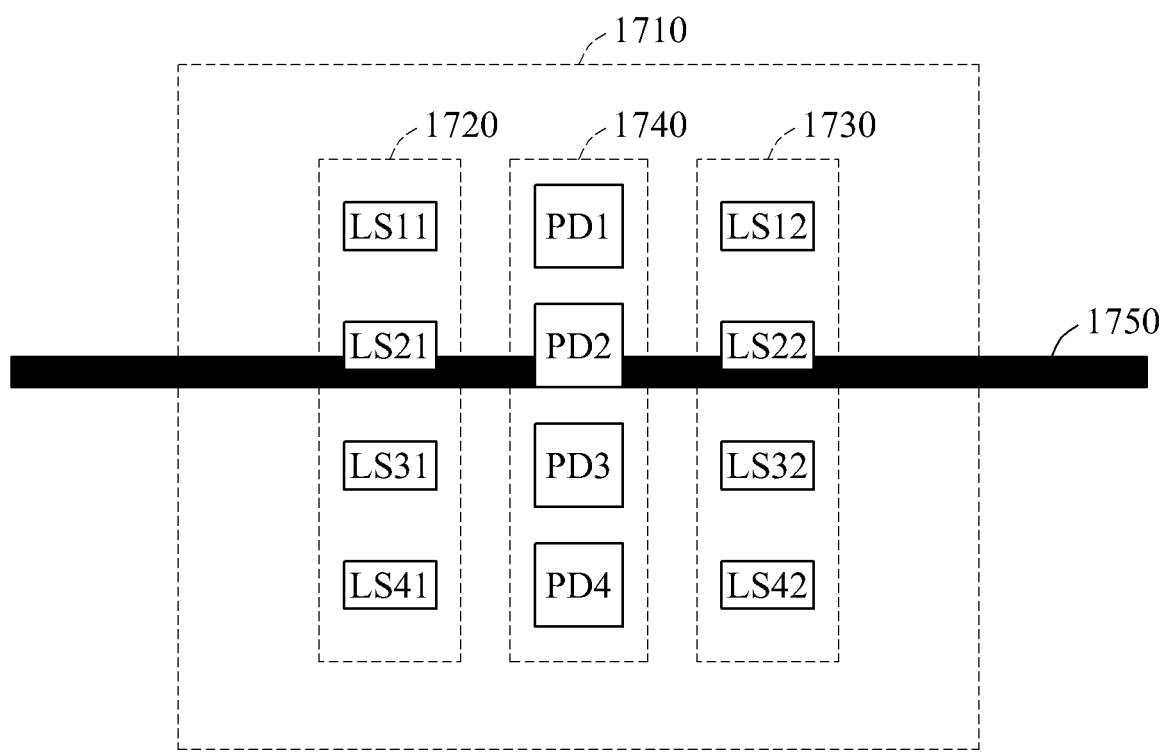
FIG. 17 is a diagram illustrating an example of an optical sensor.

FIG. 17 is a diagram illustrating an example of a structure of an optical sensor 1710.

The optical sensor 1710 senses a current measurement-based biosignal such as a PPG and a blood oxygen saturation. The optical sensor 1710 corresponds to the optical sensor 1640 of FIG. 16B. The optical sensor 1710 includes a light source unit to radiate a light signal onto a body of a user, and a light detector 1740 to detect a biosignal based on the light signal. The light source unit may include a plurality of light sources, and may have an array structure in which the light sources are arranged in a predetermined direction. In FIG. 17, as one example, the light source unit includes a first light source array 1720 and a second light source array 1730. The first light source array 1720 includes light sources LS11, LS21, LS31, and LS41. The second light source array 1730 includes light sources LS12, LS22, LS32, and LS42.

In the example in FIG. 17, the light detector 1740 is disposed between the first light source array 1720 and the second light source array 1730. The light detector 1740 includes a plurality of photo detectors, and has a structure in which the photo detectors are arranged in a predetermined direction. In FIG. 17, as one example, the light detector 1740 includes photo detectors PD1, PD2, PD3, and PD4.

Based on a physical characteristic of a user, a position of a radial artery 1750 in a wrist may vary. An optimal biosignal may be acquired using the array structure of the light source unit and the array structure of the light detector 1740. For example, when the user wears the wearable device 1510, the radial artery 1750 may be located close to the photo detector PD2. In this example, a biosignal measured by the photo detector PD2 will have a higher amplitude or fluctuation when compared to a biosignal measured by the photo detectors PD1, PD3, and PD4.

The light sources included in the first light source array 1720 and the light sources included in the second light source array 1730 may radiate light having the same wavelength or light having different wavelengths. For example, when measuring a blood oxygen saturation of the user, the light sources included in the first light source array 1720 radiate red light, and the light sources included in the second light source array 1730 radiate infrared light.

Figure 18:
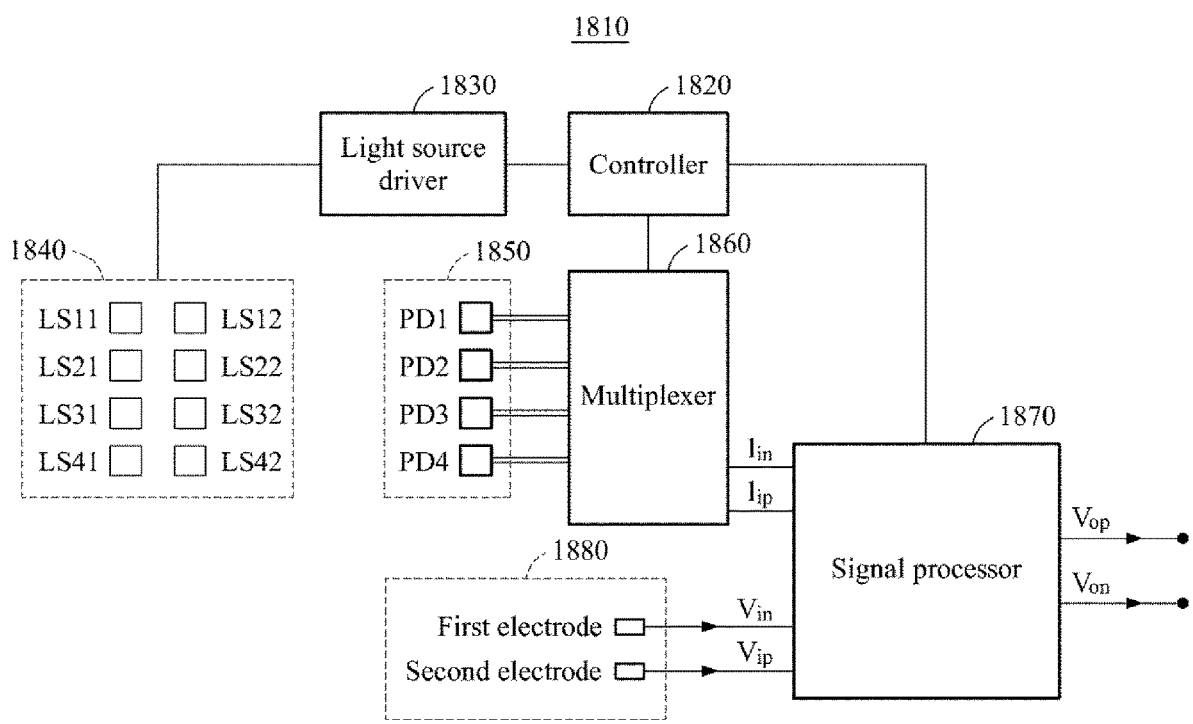
FIG. 18 is a diagram illustrating an example of a signal processing apparatus.

FIG. 18 is a diagram illustrating an example of a configuration of a signal processing apparatus 1810.

The signal processing apparatus 1810 measures various types of biosignals from a body of a user and processes the measured biosignals. The signal processing apparatus 1810 includes various sensors for measuring a biosignal. For example, the signal processing apparatus 1810 includes electrodes for measuring a voltage measurement-based biosignal, and an optical sensor for measuring a current measurement-based biosignal. The signal processing apparatus 1810 may operate in a voltage measuring mode or in a current measuring mode. Based on a measurement mode, the signal processing apparatus 1810 controls connections between internal elements of the signal processing apparatus 1810 to amplify biosignals having different attributes.

Referring to FIG. 18, the signal processing apparatus 1810 includes a light source unit 1840, a light detector 1850, a bioelectrode 1880, a signal processor 1870, and a controller 1820.

The light source unit 1840 radiates light onto the body of the user. The light source unit 1840 includes a plurality of light sources, and has a structure in which the light sources are arranged in a predetermined direction. The light sources form a plurality of light source array structures. Light sources included in each of the light source array structures may radiate light having the same wavelength, or light having different wavelengths. In the example in FIG. 18, a first light source array includes light sources LS11, LS21, LS31, and LS41, and a second light source array includes light sources LS12, LS22, LS32, and LS42. For example, the light sources LS11 and LS12 may radiate light having the same wavelength, or light having different wavelengths.

In one example, the light detector 1850 detects a first biosignal measured based on a light signal output from the light source unit 1840. For example, the first biosignal may be a PPG signal or a signal including $SpO_2$ information. The light detector 1850 includes a plurality of photo detectors, and has an array structure in which the photo detectors are arranged in a predetermined direction. In the example in FIG. 18, the light detector 1850 includes photo detectors PD1, PD2, PD3, and PD4.

The controller 1820 controls a light source driver 1830 to drive the light source unit 1840, a multiplexer 1860, and the signal processor 1870. The controller 1820 uses the multiplexer 1860 to control connections between the signal processor 1870 and the photo detectors PD1, PD2, PD3, and PD4. The photo detectors PD1, PD2, PD3, and PD4 are connected to the multiplexer 1860. The multiplexer 1860 may apply, to the signal processor 1870, predetermined biosignals, for example, first biosignals $I_{in}$ and $I_{ip}$ among a plurality of first biosignals output from the photo detectors PD1, PD2, PD3, and PD4 under a control of the controller 1820.

The bioelectrode 1880 detects a second biosignal measured based on a voltage signal. For example, the second biosignal may be an ECG signal. In the example in FIG. 18, the bioelectrode 1880 includes a first electrode and a second electrode, and detects the second biosignal measured from an electrical path through the user's body between the first electrode and the second electrode. The first electrode and the second electrode are connected to an input end of the signal processor 1870, and respectively apply signals $V_{ip}$ and $V_{in}$ to the signal processor 1870.

The signal processor 1870 amplifies the first biosignal or the second biosignal depending on a measurement mode. Signals $V_{op}$ and $V_{on}$ are output signals of the signal processor 1870. Detailed descriptions of the operations performed by the signal processor 1870 have been described with reference to FIGS. 1 through 14. The controller 1820 controls the measurement mode of the signal processor 1870, which may be a current measuring mode or a voltage measuring mode.

In the current measuring mode, the controller 1820 controls the signal processor 1870 to amplify the first biosignal. The controller 1820 controls a connection between the signal processor 1870 and the bioelectrode 1880 to prevent the signal processor 1870 from amplifying the second biosignal output from the bioelectrode 1880, and to input the first biosignal output from the light detector 1850 to the signal processor 1870 through the multiplexer 1860.

In the voltage measuring mode, the controller 1820 controls the signal processor 1870 to amplify the second biosignal. The controller 1820 uses the multiplexer 1860 to block the first biosignal output from the light detector 1850 from being input to the signal processor 1870. Also, the controller 1820 controls the signal processor to amplify the second biosignal output from the bioelectrode 1880.

Additionally, the controller 1820 may select at least one light source for measuring the biosignal from the light sources LS11 to LS42 included in the light source unit 1840. The controller 1820 may sequentially activate at least one light source among the light sources during each of a plurality of time intervals, and select a light source for measuring the first biosignal from the light sources LS11 to LS42 based on a level of a signal output from the light detector 1850 during each time interval.

In one example, the controller 1820 controls the light source driver 1830 to activate only the light sources LS11 and LS12 during a first time interval, and controls the multiplexer 1860 to apply an output signal of the photo detector PD1 to an input terminal of the signal processor 1870. During a second time interval following the first time interval, the controller 1820 activates only the light sources LS21 and LS22, and controls the multiplexer 1860 to apply an output signal of the photo detector PD2 to the input terminal of the signal processor 1870. During a third time interval following the second time interval, the controller 1820 activates only the light sources LS31 and LS32, and controls the multiplexer 1860 to apply an output signal of the photo detector PD3 to the input terminal of the signal processor 1870. During a fourth time interval provided following the third time interval, the controller 1820 activates only the light sources LS41 and LS42, and controls the multiplexer 1860 to apply an output signal of the photo detector PD4 to the input terminal of the signal processor 1870.

The controller 1820 may repetitively perform the aforementioned procedure and analyze the level of the signal output by the light detector during each time interval, thereby determining a pair of a light source and a photo detector to be used for measuring the first biosignal. The controller 1820 may operate only the determined light source and the determined photo detector, and control the multiplexer 1860 so that an output signal of the determined photo detector is applied to the input terminal of the signal processor 1870. For example, when the level of the signal output by the photo detector PD2 during the second time interval is higher than levels of the signals output by the photo detectors PD1, PD3, and PD4 during the first, third, and fourth time intervals, the controller 1820 may determine the light sources LS21 and LS22 as light sources for measuring the second biosignal, and control the multiplexer 1860 to apply an output signal of the photo detector PD2 to the signal processor 1870.

In another example, the controller 1820 may periodically perform the aforementioned procedure of determining the pair of light source and photo detector, thereby determining an optimal sensing position for measuring the first biosignal. Based on light emitting timing information of the light sources LS11 to LS42 received from the controller 1820, the signal processor 1870 may determine a time interval during which the determined light source emits light, and amplify the signal of the photo detector input to the signal processor 1870 only during the determined time interval, thereby amplifying only the signal of the determined photo detector.

The controllers 130 and 1820 in FIGS. 1 and 18, the input current compensators 210 and 450 in FIGS. 2-4 and 12, the input current compensation controller 1250 in FIG. 12, and the light source driver 1830 and the multiplexer 1860 in FIG. 18 that perform the operations described herein with respect to FIGS. 1-18 are implemented by hardware components. Examples of hardware components include controllers, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1-18. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The method illustrated in FIG. 14 that performs the operations described herein with respect to FIGS. 1-18 is performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A signal processing apparatus comprising:
   a controller configured to select a measurement mode to be one of a voltage measuring mode and a current measuring mode;
   a voltage input circuit configured to receive an input voltage measured from a body of a user;
   a current input circuit configured to receive an input current measured from the body of the user;
   an amplifier configured to amplify one of the measured input voltage and the measured input current at a time, dependent on the selected measurement mode; and
   the controller configured to, dependent on the selected measurement mode, control a connection between the voltage input circuit and the amplifier, or control a connection between the current input circuit and the amplifier.

2. The apparatus of claim 1, wherein the controller is further configured to block the connection between the current input circuit and the amplifier and connect the voltage input circuit to the amplifier in the voltage measuring mode.

3. The apparatus of claim 1, wherein the controller is further configured to block the connection between the voltage input circuit and the amplifier and connect the current input circuit to the amplifier in the current measuring mode.

4. The apparatus of claim 1, wherein the current input circuit is further configured to adjust, using an input current compensator different from the amplifier, a level of the input current in response to the level of the input current being greater than a preset value and output the input current having the adjusted level in the current measuring mode.

5. The apparatus of claim 1, wherein the input voltage is an electrocardiogram (ECG) signal, and the input current is a photoplethysmogram (PPG) signal.

6. A signal processing apparatus comprising:
   a controller configured to select a measurement mode to be one of a voltage measuring mode and a current measuring mode;

a voltage input circuit configured to receive an input voltage measured from a user;

a current input circuit configured to receive an input current measured from the user;

the controller configured to, dependent on the selected measurement mode, control a first connection between the voltage input circuit and an amplifier, or control a second connection between the current input circuit and the amplifier; and the amplifier configured to selectively amplify one of the measured input voltage and the measured input current at a time, dependent on the selected measurement mode, using the controlling of the first connection or the second connection.

* * * * *